US012723234B2

(12) United States Patent
Dani et al.

(10) Patent No.: US 12,723,234 B2
(45) Date of Patent: Sep. 1, 2026

(54) METHOD FOR THE IN VITRO OR EX VIVO AMPLIFICATION OF HUMAN ADIPOSE TISSUE STEM CELLS

(71) Applicants: UNIVERSITÉ CÔTE D'AZUR, Nice (FR); INSTITUT NATIONAL DE LA SANTÉ ET DE LA RECHERCHE MÉDICALE, Paris (FR); CENTRE NATIONAL DE LA RECHERCHE SCIENTIFIQUE (CNRS), Paris (FR); CHU DE NICE, Nice (FR)

(72) Inventors: Christian Dani, Nice (FR); Alain Doglio, Saint André de la Roche (FR); Vincent Dani-Davesne, Nice (FR); Philippe Letertre, Colle sur Loup (FR)

(73) Assignees: UNIVERSITÉ CÔTE D'AZUR, Nice (FR); INSTITUT NATIONAL DE LA SANTÉ ET DE LA RECHERCHE MÉDICALE, Paris (FR); CENTRE NATIONAL DE LA RECHERCHE SCIENTIFIQUE (CNRS), Paris (FR); CHU DE NICE, Nice (FR)

( * ) Notice: Subject to any disclaimer, the term of this patent is extended or adjusted under 35 U.S.C. 154(b) by 980 days.

(21) Appl. No.: 17/421,840

(22) PCT Filed: Jan. 13, 2020

(86) PCT No.: PCT/EP2020/050720

§ 371 (c)(1),
(2) Date: Jul. 9, 2021

(87) PCT Pub. No.: WO2020/144381

PCT Pub. Date: Jul. 16, 2020

(65) Prior Publication Data

US 2022/0098552 A1 Mar. 31, 2022

(30) Foreign Application Priority Data

Jan. 11, 2019 (FR) .................................... 1900287

(51) Int. Cl.

| | |
|---|---|
| ***C12N 5/077*** | (2010.01) |
| ***A61L 27/36*** | (2006.01) |
| ***A61L 27/38*** | (2006.01) |
| ***C12M 1/00*** | (2006.01) |
| ***C12N 5/071*** | (2010.01) |

(52) U.S. Cl.

CPC .......... *C12N 5/0653* (2013.01); *A61L 27/362* (2013.01); *A61L 27/3633* (2013.01); *A61L 27/3834* (2013.01); *C12M 23/14* (2013.01); *C12N 5/0697* (2013.01); *A61L 2430/34* (2013.01); *A61L 2430/40* (2013.01); *C12N 2501/105* (2013.01); *C12N 2501/11* (2013.01); *C12N 2501/115* (2013.01); *C12N 2501/39* (2013.01); *C12N 2501/91* (2013.01); *C12N 2501/999* (2013.01); *C12N 2506/1384* (2013.01); *C12N 2513/00* (2013.01); *C12N 2533/54* (2013.01); *C12N 2533/90* (2013.01)

(58) Field of Classification Search

CPC . C12N 5/0653; A61L 27/362; A61L 27/3633; A61L 27/3834; A61L 2430/34; A61L 2430/40

See application file for complete search history.

(56) References Cited

U.S. PATENT DOCUMENTS

| | | | |
|---|---|---|---|
| 2013/0059383 A1* | 3/2013 | Dijkhuizen Borgart .................... C12M 25/16 435/297.2 | |
| 2015/0275177 A1 | 10/2015 | West et al. | |
| 2017/0021058 A1 | 1/2017 | Huang et al. | |
| 2018/0216070 A1 | 8/2018 | Deschaseaux et al. | |
| 2023/0279355 A1 | 9/2023 | Dani et al. | |

FOREIGN PATENT DOCUMENTS

| | | |
|---|---|---|
| CN | 109010920 A | 12/2018 |
| JP | 2015-213496 A | 12/2015 |

OTHER PUBLICATIONS

Yao, Yao, et al. "Adipose extracellular matrix/stromal vascular fraction gel: a novel adipose tissue-derived injectable for stem cell therapy." Plastic and Reconstructive Surgery 139.4 (2017): 867-879. (Year: 2017).*

Frantz, Christian, Kathleen M. Stewart, and Valerie M. Weaver. "The extracellular matrix at a glance." Journal of cell science 123.24 (2010): 4195-4200. (Year: 2010).*

Choi, Ji Suk, et al. "Human extracellular matrix (ECM) powders for injectable cell delivery and adipose tissue engineering." Journal of Controlled Release 139.1 (2009): 2-7. (Year: 2009).*

Harvestine, Jenna N., et al. "Cell-secreted extracellular matrix, independent of cell source, promotes the osteogenic differentiation of human stromal vascular fraction." Journal of Materials Chemistry B 6.24 (2018): 4104-4115. (Year: 2018).*

Gentile, Pietro, et al. "Comparing different nanofat procedures on scars: role of the stromal vascular fraction and its clinical implications." Regenerative medicine 12.8 (2017): 939-952. (Year: 2017).*

Bellei, Barbara, et al. "Maximizing non-enzymatic methods for harvesting adipose-derived stem from lipoaspirate: technical considerations and clinical implications for regenerative surgery." Scientific reports 7.1 (2017): 10015. (Year: 2017).*

(Continued)

*Primary Examiner* — Teresa E Knight
*Assistant Examiner* — Michael Angelo Riga
(74) *Attorney, Agent, or Firm* — Seckel IP, PLLC

(57) ABSTRACT

The method for in vitro or ex vivo amplification of human adipose tissue stem cells includes: —extracting a stromal vascular fraction of a human adipose tissue including endothelial cells of the human adipose tissue vascular network and human adipose tissue stem cells, and an extracellular matrix of the human adipose tissue, the extracellular matrix including endothelial cells of the human adipose tissue vascular network, human adipose tissue stem cells and collagen; —mixing the stromal vascular fraction and the extracellular matrix; and —culturing the mixture obtained in the preceding step, in suspension, in a culture medium.

10 Claims, 17 Drawing Sheets

(56) References Cited

OTHER PUBLICATIONS

Scherberich, Arnaud, et al. "Three-dimensional perfusion culture of human adipose tissue-derived endothelial and osteoblastic progenitors generates osteogenic constructs with intrinsic vascularization capacity." Stem cells 25.7 (2007): 1823-1829. (Year: 2007).*
Shin, Jihoon, et al. "Regulation of dipeptidyl peptidase-4, its substrate chemokines, and their receptors in adipose tissue of ob/ob mice." Hormone and Metabolic Research 49.05 (2017): 380-387. (Year: 2017).*
International Search Report and Written Opinion dated Apr. 17, 2020 in counterpart application No. PCT/EP2020/050720; in English (total 32 pages).
Yao et al., "Adipose Extracellular Matrix/Stromal Vascular Fraction Gel : A Novel Adipose Tissue-Derived Injectable for Stem Cell Therapy", Plastic and Reconstructive Surgery, 2017, vol. 139, No. 4, pp. 867-879 (in English; D1 cited in the ISR).
Choi et al., "Human extracellular matrix (ECM) powders for injectable cell delivery and adipose tissue engineering", Journal of Controlled Release, 2009, vol. 139, No. 1, pp. 2-7 (in English; D2 cited in the ISR).
Spiekman et al., "The power of fat and its adipose-derived stromal cells: emerging concepts for fibrotic scar treatment : Adipose tissue and ADSC for fibrotic scar treatment", Journal of Tissue Engineering and Regenerative Medicine, 2017, vol. 11, No. 11, pp. 3220-3235 in English; D4 cited in the ISR.
Bora et al., "Adipose tissue-derived stromal vascular fraction in regenerative medicine: a brief review on biology and translation", Stem Cell Research & Therapy, 2017, vol. 8, No. 1, pp. 1-10 (in English; D5 cited in the ISR).
JP Office Action dated Dec. 26, 2023 in counterpart application No. JP2021-539468; with English translation (total 8 pages).
Yao et al., "Adipose Extracellular Matrix/Stromal Vascular Fraction Gel: A Novel Adipose Tissue-Derived Injectable for Stem Cell Therapy", Plastic and Reconstructive Surgery, 2017, vol. 139, pp. 867-879 (in English; D1 cited in the JP Office Action).
EP Office Action dated Jun. 12, 2024 in counterpart application No. EP20700217.1; with English translation (total 13 pages).
Sun et al., "Adipose Extracellular Matrix/Stromal Vascular Fraction Gel Secretes Angiogenic Factors and Enhances Skin Wound Healing in a Murine Model", BioMed Research International, vol. 2017, Article IDS 3105780, pp. 1-11 (in English; D6 cited in the EP Office Action).
International Search Report and Written Opinion dated Oct. 12, 2021 in application No. PCT/EP2021/069888, corresponding to co-pending U.S. Appl. No. 18/016, 128; w/English partial translation and partial machine translation (total 27 pages) (note: Yao, D2, Choi, D3, CN109010920, D4, Spiekman, D5, Bora, D6, and WO2020144381, D9 (PCT pub. of this application) cited in the ISR, are not listed in this IDS since they are already of record in this application).
Merrick et al., "Supplementary materials for Identification of a mesenchymal progenitor cell hierarchy in adipose tissue", Science, vol. 364, No. 6438, Apr. 25, 2019 (Supplementary materials, Figs. S1-S23) (total 24 pages) (note: in English; D7 cited in the ISR of co-pending U.S. Appl. No. 18/016,128).
Merrick et al., "Identification of a mesenchymal progenitor cell hierarchy in adipose tissue", Science, vol. 364, No. 6438, Apr. 25, 2019, pp. 1-25 (note: in English; D8 cited in the ISR of co-pending U.S. Appl. No. 18/016,128).
JP Office Action dated Jul. 1, 2025 in application No. JP 2023-502756, counterpart of co-pending U.S. Appl. No. 18/016,128; w/English machine translation (total 9 pages) (note: Yao 2018, D1 cited in the JP Office Action, is not listed in this IDS since it is already of record).
Su et al., "A renewable source of human beige adipocytes for development of therapies to treat metabolic syndrome", Cell Report, vol. 25, No. 11, 2018, pp. 3215-3228, e1-e9 (total 24 pages) (note: in English; D2 cited in the JP Office Action dated Jul. 1, 2025 in application JP 2023-502756, counterpart of co-pending U.S. Appl. No. 18/016,128).
Condé-Green et al., "Influence of decantation, washing and centrifugation on adipocyte and mesenchymal stem cell content of aspirated adipose tissue: A comparative study", J. Plast. Reconstr. Aesthet. Surg., 63 (2010):1375-1381.
Sforza et al., "Mechanical isolation of stromal vascular fraction from adipose tissue: methods and cellular outcomes: a systematic review and meta-analysis", Stem Cell Research & Therapy, 16:560(2025):1-12.

* cited by examiner

METHOD FOR THE IN VITRO OR EX VIVO AMPLIFICATION OF HUMAN ADIPOSE TISSUE STEM CELLS

CROSS-REFERENCE TO RELATED APPLICATION

This application is the US national stage of international application No. PCT/EP2020/050720 filed Jan. 13, 2020, and claims priority of French patent application No. FR1900287 filed Jan. 11, 2019, the content of which is hereby incorporated by reference herein in its entirety.

TECHNICAL FIELD OF THE INVENTION

The present invention relates to a method for the in vitro or ex vivo amplification of human adipose tissue stem cells. It further relates to a method for the in vitro or ex vivo amplification of differentiated cells, an extracellular matrix, a composition comprising a mixture of an extracellular matrix and a stromal vascular fraction, a use of the extracellular matrix or of the composition comprising a mixture of the extracellular matrix and the stromal vascular fraction, and differentiated cells obtained according to the method of the invention for use thereof.

PRIOR ART

Cell therapy consists of a cell graft aimed at restoring the functions of a tissue or an organ when they are impaired by an accident, a disease or ageing. It enables the long-term treatment of a patient thanks to a single injection of so-called "therapeutic" cells. These cells are obtained, in particular, from multipotent stem cells from the patient themselves.

Lipofilling is a particular cell therapy technique for transferring fat cells, or adipocytes, from one area of the body to another in order to remodel the body or face.

To date, only the adipocytes present in certain adipose sites are used for cell therapy and, more particularly, for lipofilling. However, depending on the circumstances, the quantity of adipocytes available from a patient can be limiting. For example, when a patient has a body mass index that is too low or has undergone chemotherapy, they may not have enough adipose tissue to perform lipofilling.

In this context, there is a need to produce autologous adipocytes and, hence, to develop cell amplification methods for obtaining large quantities of therapeutic grade adipocytes with a view, in particular, to lipofilling.

The standard procedure, for isolating and amplifying adipocyte precursors from adipose tissue samples, involves enzymatic separation followed by the two-dimensional (2D) expansion thereof by binding to the plastic of culture dishes. This procedure is costly, time-consuming, and requires numerous handling operations which increase contamination risks. Furthermore, it induces a destruction of the three-dimensional structure of the tissue, as well as the loss of cell types of interest such as endothelial cells which play a key role both for graft vascularization and adipocyte physiology.

Non-enzymatic separation of adipose tissue, most frequently based on a mechanical process, makes it possible to isolate adipocyte precursors. This type of separation is emerging as a much less costly, quicker alternative method, which has indisputable advantages for the manufacture of a product according to therapeutic grade production standards (reduced exposure to external products or contaminants). On the other hand, the non-enzymatic separation methods described to date are not satisfactory as the number of adipocyte precursors obtained is low compared to enzymatic separation. This then requires the 2D amplification thereof on a culture dish. Furthermore, the endothelial cells, the extracellular matrix as well as the three-dimensional structure of adipose tissue are lost at the end of the process.

Different synthetic matrices have been proposed in order to inoculate the adipocyte precursors therein and thus attempt to best reconstitute the structure of adipose tissue. The matrix also serves to orient adipocyte precursors in vitro to a non-adipose (essentially bone or cartilaginous) cell type before implantation. Decellularized adipose tissue has also been proposed to increase precursor differentiation and better imitate the structure of adipose tissue. The manufacture of all these types of matrices requires numerous steps involving enzymatic reactions or long chemical treatments. Furthermore, decellularized tissue, by definition, loses these endogenous cells but also loses the factors of therapeutic interest which are anchored on the native matrix, which reduces the clinical value of this type of matrix. Non-decellularized adipose tissue enriched with adipocyte precursors (previously isolated by enzymatic separation) followed by 2D amplification has recently been proposed as a matrix for better bone reconstruction. The time to generate this biological matrix is long, requires three weeks of in vitro culture, and does not allow adipocyte precursor amplification. The authors only highlighted the benefit for bone repair.

Three-dimensional (3D) suspension culture represents an alternative method of choice to the standard 2D method as it essentially makes it possible to retain the structure and the intrinsic qualities of the tissue. This advantage is important because, for example, the lack of a relevant human model which best imitates adipose tissue in vitro is a major limitation during preclinical phase trials for the discovery of novel medicinal products effective in combatting obesity and associated metabolic diseases such as type 2 diabetes and cardiovascular diseases. Furthermore, 3D culture is feasible in a closed system which decreases handling operations and contamination risks.

SUMMARY OF THE INVENTION

In view of the above, a technical problem addressed by the present invention is that of obtaining in vitro or ex vivo a large quantity of human adipose tissue stems cells or differentiated cells, of therapeutic grade.

A first object of the solution of the invention to this technical problem is a method for the in vitro or ex vivo amplification of human adipose tissue stem cells, comprising the following steps: extracting a stromal vascular fraction of a human adipose tissue comprising endothelial cells of the human adipose tissue vascular network and human adipose tissue stem cells, and an extracellular matrix of said human adipose tissue, said extracellular matrix comprising endothelial cells of the human adipose tissue vascular network, human adipose tissue stem cells and collagen; mixing said stromal vascular fraction and said extracellular matrix; and culturing the mixture obtained in the preceding step, in suspension, in a culture medium.

Thus, the stromal vascular fraction suspension culture, enabled thanks to the presence of the extracellular matrix, enables a 3D amplification, giving access to a large number of cells and thus limiting handling operations which increase the contamination risks.

Advantageously, —the extraction of the extracellular matrix comprises a step of non-enzymatic separation and, in particular, the extraction of the extracellular matrix comprises a step of mechanical separation; —the extraction of the stromal vascular fraction and the extracellular matrix comprises the following steps: centrifuging the human adipose tissue to obtain at least two distinct fractions, a fraction A comprising a centrifuged extracellular matrix, and the stromal vascular fraction; and mechanically separating the fraction A to obtain the extracellular matrix; —the collagen of the extracellular matrix is type I collagen and type III collagen; and —the culture of the mixture of said stromal vascular fraction and said extracellular matrix comprises the following steps: transferring said mixture sterilely into a bag of suspension culture comprising culture medium; amplifying said mixture forming cellular aggregates; and mechanically separating said cellular aggregates.

According to a second object, the invention relates to a method for the in vitro or ex vivo amplification of differentiated cells comprising the following steps: extracting a stromal vascular fraction of a human adipose tissue comprising endothelial cells of the human adipose tissue vascular network and human adipose tissue stem cells, and an extracellular matrix of said human adipose tissue, said extracellular matrix comprising endothelial cells of the human adipose tissue vascular network, human adipose tissue stem cells and collagen; mixing said stromal vascular fraction and said extracellular matrix; culturing the mixture obtained in the preceding step, in suspension, in a culture medium; and inducing a differentiation of the adipose tissue stem cells to obtain differentiated cells.

Advantageously, —the differentiated cells are adipocytes or osteoblasts, preferably adipocytes; —the extraction of the extracellular matrix comprises a step of non-enzymatic separation, in particular the extraction of the extracellular matrix comprises a step of mechanical separation; —the extraction of the stromal vascular fraction and the extracellular matrix comprises the following steps: centrifuging the human adipose tissue to obtain at least two distinct fractions, a fraction A comprising a centrifuged extracellular matrix, and the stromal vascular fraction; and mechanically separating the fraction A to obtain the extracellular matrix; —the collagen of the extracellular matrix is type I collagen and type III collagen; and —the culture of the mixture of stromal vascular fraction and said extracellular matrix comprises the following steps: transferring said mixture sterilely into a bag of suspension culture comprising culture medium; amplifying said mixture forming cellular aggregates; and mechanically separating said cellular aggregates.

According to a third object, the invention relates to an isolated extracellular matrix capable of being obtained according to the method defined above, comprising endothelial cells of the human adipose tissue vascular network, human adipose tissue stem cells, and collagen.

Advantageously —the collagen is type I collagen and type III collagen; —the extracellular matrix further comprises fibronectin.

According to a fourth object, the invention relates to a composition comprising the mixture of the extracellular matrix and the stromal vascular fraction as defined above, the extracellular matrix comprising endothelial cells of the human adipose tissue vascular network, human adipose tissue stem cells, and collagen, and the stromal vascular fraction comprising endothelial cells of the adipose tissue vascular network and adipose tissue stem cells.

Advantageously —the collagen is type I collagen and type III collagen; —the extracellular matrix further comprises fibronectin.

According to a fifth object, the invention relates to the in vitro use of the extracellular matrix as defined above or the in vitro use of the composition as defined above for screening pharmacological active substances against obesity and associated metabolic diseases.

According to a fifth object, the invention relates to differentiated cells obtained according to the method defined above intended for use, or for the use thereof, in cell therapy, in particular in plastic and reparative surgery and, more particularly, for lipofilling.

BRIEF DESCRIPTION OF THE FIGURES

The invention will be better understood on reading the following non-restrictive description, drafted with reference to the appended drawings, wherein:

In FIG. 17A, a non-separated adipose tissue shows no proliferating cells. In FIG. 17B, the composition shows proliferating cells, the nuclei of the proliferating cells being represented in white in this figure;

DETAILED DESCRIPTION OF THE INVENTION

Figure 1A:
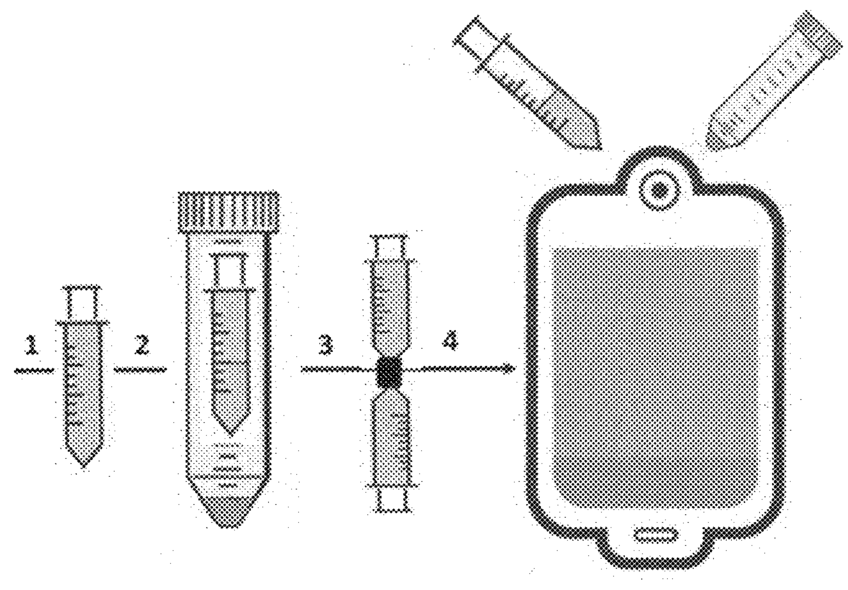
FIG. 1A represents schematically the necessary and sufficient steps for extracting an extracellular matrix and a stromal vascular fraction (steps 1 to 3), and placing them in coculture (step 4), according to the invention.

Adipose tissue is supplied to carry out the Invention.

A first object of the invention is a method for the in vitro or ex vivo amplification of human adipose tissue stem cells, comprising the following steps: extracting a stromal vascular fraction of a human adipose tissue comprising endothelial cells of the human adipose tissue vascular network and human adipose tissue stem cells, and an extracellular matrix of said human adipose tissue, said extracellular matrix comprising endothelial cells of the human adipose tissue vascular network, human adipose tissue stem cells and collagen; mixing said stromal vascular fraction and said extracellular matrix; and culturing the mixture obtained in the preceding step, in suspension, in a culture medium. This method is also hereinafter referred to as the "ExAdEx method" (for Ex vivo Adipocytes Expansion).

According to the present invention, "stromal vascular fraction" denotes the cells present in a human adipose tissue sample. This stromal vascular fraction comprises endothelial cells of the human adipose tissue vascular network and human adipose tissue stem cells.

According to the invention, "extracellular matrix" denotes a bioactive matrix, i.e., a matrix which comprises different proteins of adipose tissue and endogenous cells. This extracellular matrix enables 3D cell amplification, i.e., three-dimensional cell proliferation. The extracellular matrix of the invention is also referenced hereinafter as "EndoStem-Matrix" or "EndoStem matrix".

The proteins of the extracellular matrix of the adipose tissue comprise collagen. This collagen is type I and type III. The proteins of the extracellular matrix of the adipose tissue further comprise fibronectin.

The extraction of the extracellular matrix comprises a step of non-enzymatic separation, in particular the extraction of the extracellular matrix comprises a step of mechanical separation. The "mechanical separation" of the invention makes it possible to keep the structure of the extracellular matrix intact whereas an enzymatic digestion generally involves collagenase which destroys it. The mechanical separation thus helps maintain the "vasculature" and the micro-structure of the extracellular matrix, which accordingly has a similar organization to the organization of adipose tissue in vivo.

The extraction of the stromal vascular fraction and the extracellular matrix comprises the following steps: centrifuging human adipose tissue to obtain at least two separate fractions, a fraction A comprising a centrifuged extracellular matrix, and the stromal vascular fraction; and mechanically separating the fraction A to obtain the extracellular matrix.

The step of centrifuging human adipose tissue furthermore makes it possible to remove oil, blood and anesthetic fluid contained in the human adipose tissue supplied. This step also makes it possible to remove saline solution obtained from preliminary washes of the human adipose tissue supplied.

In a particular embodiment, the extraction of the stromal vascular fraction and the extracellular matrix comprises the following steps: centrifuging human adipose tissue to obtain at least two separate fractions, a fraction A comprising a centrifuged extracellular matrix and a fraction B comprising endothelial cells of the human adipose tissue vascular network and human adipose tissue stem cells; mechanically separating the fraction A to obtain a fraction A' comprising a separated extracellular matrix; centrifuging the fraction A' to obtain at least the extracellular matrix and a fraction B' comprising endothelial cells of the human adipose tissue vascular network and human adipose tissue stem cells; and mixing the fractions B and B' to obtain the stromal vascular fraction.

In this embodiment, the step of centrifuging human adipose tissue furthermore makes it possible to remove oil, blood and anesthetic fluid contained in the human adipose tissue supplied. This step also makes it possible to remove saline solution obtained from preliminary washes of the human adipose tissue supplied. Centrifuging the fraction A' furthermore makes it possible to remove any oil and saline solution residues. This step of centrifuging the fraction A' is optional.

The culture of the mixture of said stromal vascular fraction and said extracellular matrix comprises the following steps: transferring said mixture sterilely into a bag of suspension culture comprising culture medium; amplifying said mixture forming cellular aggregates; and mechanically separating said cellular aggregates.

Transferring "sterilely", according to the invention, is a transfer, preferably, carried out in a closed system. This sterile transfer makes it possible to limit the number of contaminants during the cell culture. The mechanical separation of the aggregates formed during the amplification does not require opening the system, thus limiting the exposure of the cellular products to potential contamination of the culture by elements from the environment.

In an embodiment, the culture medium, in the bag of suspension culture, is an EGM+ medium. This culture medium comprises the base medium for proliferating the endothelial cells (EGM) enriched with Epidermal Growth Factor (EGF), Basic Growth Factor (FGF2), Insulin-like Growth Factor, Vascular Endothelial Growth Factor 165, ascorbic acid, heparin and hydrocortisone (EGM+). The EGM+ medium also enables the amplification of the adipocytic stem cells without altering their differentiation capacity into adipocytes.

The method of the invention enables an amplification of the number of adipose tissue stem cells with an amplification factor greater than 10, advantageously greater than 20, in particular greater than 30, preferably greater than 35. The amplification factor is the ratio between the number of cells obtained after culturing the isolated SVF in the presence of said extracellular matrix and the number of cells before the invention. In a particular embodiment described in example 2, the method of the invention has an amplification factor of 36 in 8 days.

According to a second object, the invention relates to a method for the in vitro or ex vivo amplification of differentiated cells comprising the following steps: in vitro or ex vivo amplification of human adipose tissue stem cells as defined above; and inducing a differentiation of the adipose tissue stem cells to obtain differentiated cells.

More specifically, the method for the in vitro or ex vivo amplification of differentiated cells therefore comprises the following steps: extracting a stromal vascular fraction of a human adipose tissue comprising endothelial cells of the human adipose tissue vascular network and human adipose tissue stem cells, and an extracellular matrix of said human adipose tissue, said extracellular matrix comprising endothelial cells of the human adipose tissue vascular network, human adipose tissue stem cells and collagen; mixing said stromal vascular fraction and said extracellular matrix; culturing the mixture obtained in the preceding step, in suspension, in a culture medium; and inducing a differentiation of the adipose tissue stem cells to obtain differentiated cells.

According to the invention, the differentiated cells are adipocytes or osteoblasts. Preferably, the differentiated cells are adipocytes.

The method for the in vitro or ex vivo amplification of differentiated cells comprising the steps associated with the in vitro or ex vivo amplification of adipose tissue stem cells, the details given above of the method for the in vitro or ex vivo amplification method of adipose tissue stem cells also apply for the method for the in vitro or ex vivo amplification of differentiated cells.

In particular, the extraction of the extracellular matrix comprises a step of non-enzymatic separation, in particular the extraction of the extracellular matrix comprises a step of mechanical separation.

In an embodiment, the extraction of the stromal vascular fraction and the extracellular matrix comprises the following steps: centrifuging human adipose tissue to obtain at least two separate fractions, a fraction A comprising a centrifuged extracellular matrix, and the stromal vascular fraction; and mechanically separating the fraction A to obtain the extracellular matrix.

In a further embodiment, the extraction of the stromal vascular fraction and the extracellular matrix comprises the following steps: centrifuging human adipose tissue to obtain at least two separate fractions, a fraction A comprising a centrifuged extracellular matrix and a fraction B comprising endothelial cells of the human adipose tissue vascular network and human adipose tissue stem cells; mechanically separating the fraction A to obtain a fraction A' comprising a separated extracellular matrix; centrifuging the fraction A' to obtain at least the extracellular matrix and a fraction B' comprising endothelial cells of the human adipose tissue vascular network and human adipose tissue stem cells; and mixing the fractions B and B' to obtain the stromal vascular fraction.

The collagen of the extracellular matrix comprises type I collagen and type III collagen detected by Picro-Sirius Red staining.

The culture of the mixture of said stromal vascular fraction and said extracellular matrix comprises the following steps: transferring said mixture sterilely into a bag of suspension culture comprising culture medium; amplifying said mixture forming cellular aggregates; and mechanically separating said cellular aggregates.

According to a third object, the invention relates to an isolated extracellular matrix capable of being obtained according to the method defined above, comprising endothelial cells of the human adipose tissue vascular network, human adipose tissue stem cells, and collagen.

The collagen is type I collagen and type III collagen. The extracellular matrix further comprises fibronectin.

According to a fourth object, the invention relates to a composition comprising the mixture of the extracellular matrix and the stromal vascular fraction as defined above, the extracellular matrix comprising endothelial cells of the human adipose tissue vascular network, human adipose tissue stem cells, and collagen, and the stromal vascular fraction comprising endothelial cells of the adipose tissue vascular network and adipose tissue stem cells.

The collagen is type I collagen and type III collagen. The extracellular matrix further comprises fibronectin.

According to a fifth object, the invention relates to the in vitro use of the extracellular matrix as defined above or the in vitro use of the composition as defined above for screening pharmacological active substances against obesity and associated metabolic diseases such as type 2 diabetes and cardiovascular diseases.

According to a fifth object, the invention relates to differentiated cells obtained according to the method defined above intended for use, or for the use thereof, in cell therapy, in particular in plastic and reparative surgery and more particularly for lipofilling.

In the case of use in plastic and reparative surgery, the extracellular matrix is an autologous matrix, which contains, by definition, cells specific to the patient from whom the adipose tissue is obtained.

For use for lipofilling, the differentiated cells obtained with the method of the invention are adipocytes.

EXAMPLES

Example 1. Mechanical Extraction a) Mechanical Extraction Method with a View to Characterizing the Cell and Matrix Populations During the Process The mechanical extraction of the stromal vascular fraction and the extracellular matrix, from a sample of adipose tissue from a human donor, can be carried out according to the following steps (FIG. 1B):

1. Sampling adipose tissue by suction in a 10 cc sterile syringe equipped with a 2 mm Coleman cannula under −20 kPa negative pressure.
2. In order to separate the different phases, the syringe is centrifuged at 1600 rcf (relative centrifugal force), for 3 min in the collection tube. The oil fraction and the blood and anesthetic fluid fraction are removed. The pelleted fraction is retained.
3. One unit of saline solution is injected into the syringe, followed by incubation for 30 min at 37° C. with stirring. The syringe is centrifuged at 1600 rcf, for 3 min in the collection tube. The saline solution fraction and the oil fraction are removed. The pelleted fraction is retained.
4. The syringe is connected to another make Luer-Lock type syringe by a Tulip® type connector in order to perform the separation of the tissue by emulsification. Three types of Tulip® connector, 2.4 mm, 1.4 mm and 1.2 mm, are successively used, on 30 passages.
5. One unit of saline solution is injected into the syringe, followed by incubation for 30 min at 37° C. with stirring. The syringe is centrifuged at 1600 rcf for 3 min in the collection tube. The saline solution fraction and the oil fraction are removed. The pelleted fraction is retained.
6. The contents of the syringe and the contents of the collection tubes previously cleared of blood cells are transferred via sterile connection into a culture bag containing EGM+ culture medium at 37° C. for the expansion phase.

In step 4 above of separating the tissue, a connector of a brand other than the Tulip® brand can be used. The number of connectors used is between 1 and 5. The number of passages via these connectors used is between 10 and 50.

b) Characterizing the Cell Populations Obtained

The method described above makes it possible to sequentially extract the stromal vascular fraction into 3 cell populations. These cell populations are characterized in particular by optical microscopy and by fluorescence microscopy.

Figure 2:
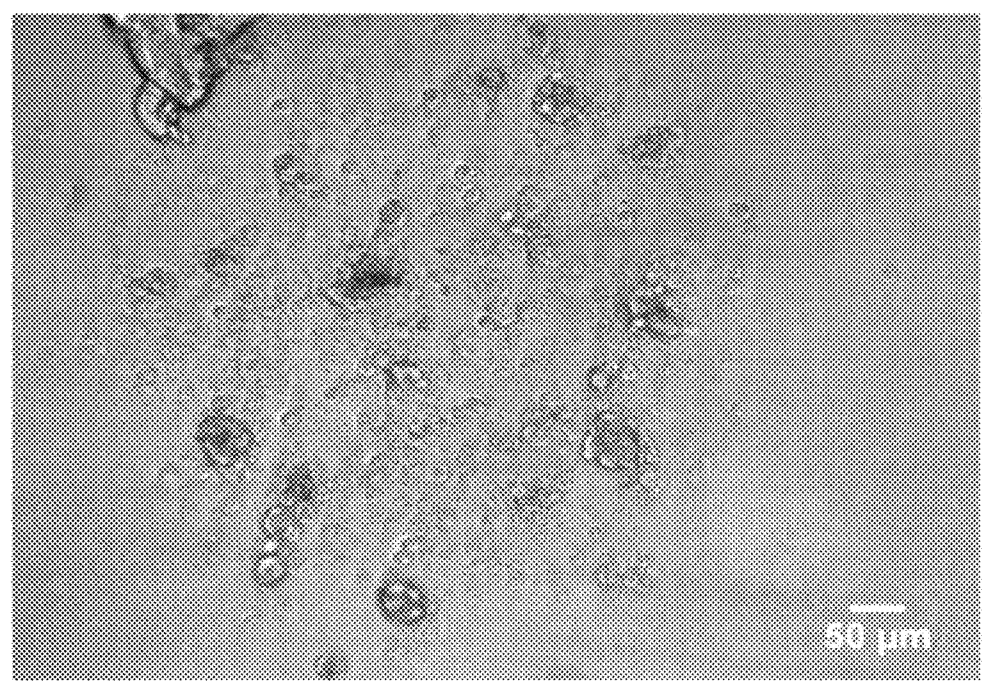
FIG. 2 represents the cell population C1 in Endothelial Growth Medium culture medium supplemented with growth factors (EGM+), in suspension, consisting of a majority of endothelial type cells.
Figure 3A:
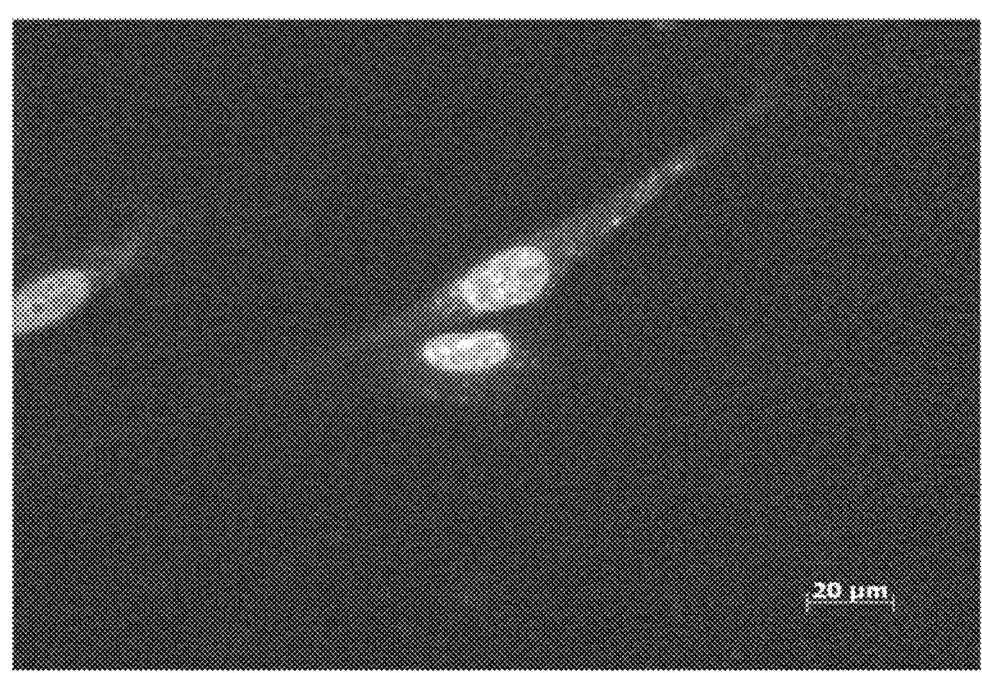
FIG. 3A shows the CD31+ (endothelial cell marker) immunofluorescent labelling of the cell population C1 in adherent culture.
Figure 3B:
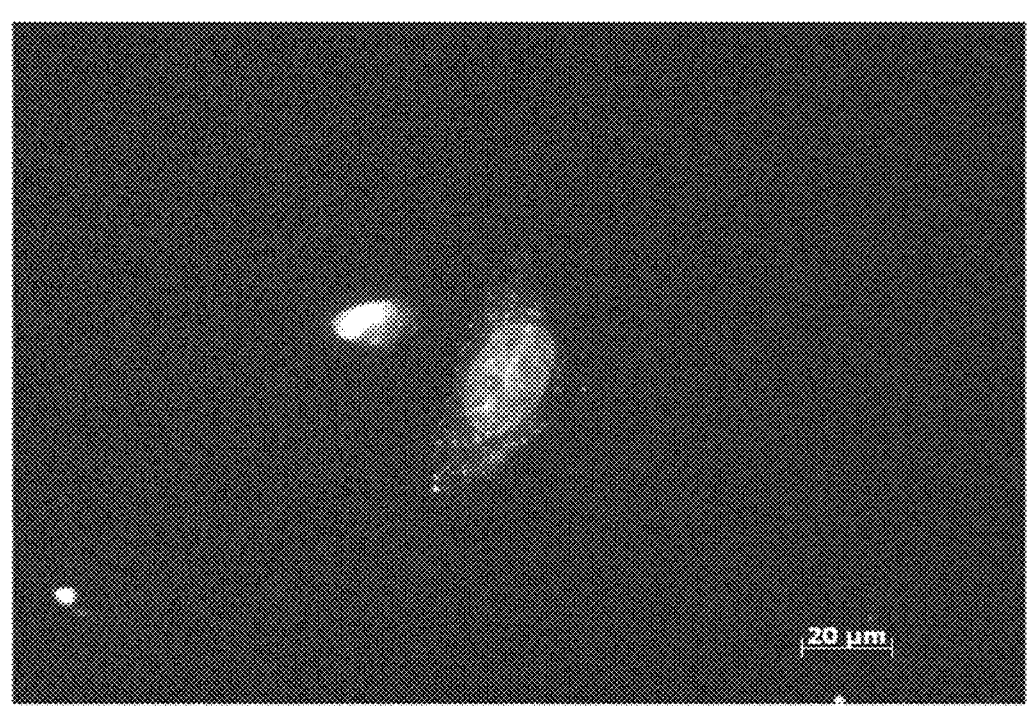
FIG. 3B shows the PDGFRa+ (adipocyte stem cell marker) immunofluorescent labelling of the cell population C1 in adherent culture.

The cell population obtained in step 2, herein called C1, is composed of a majority of CD31+ endothelial type cells (FIG. 2 and FIG. 3).

Figure 4:
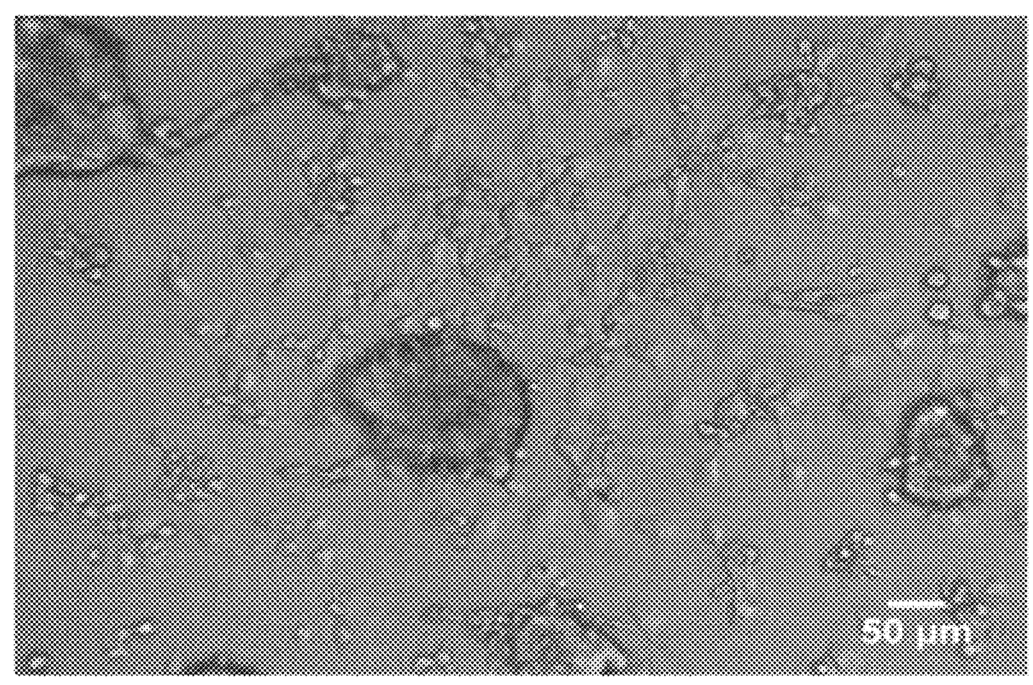
FIG. 4 illustrates the cell population C2 in EGM+ culture medium in suspension showing the formation of a capillary type network consisting of CD31+ endothelial cells and presence of aggregates consisting of PDGFRa+ adipose tissue stem cells.
Figure 6A:
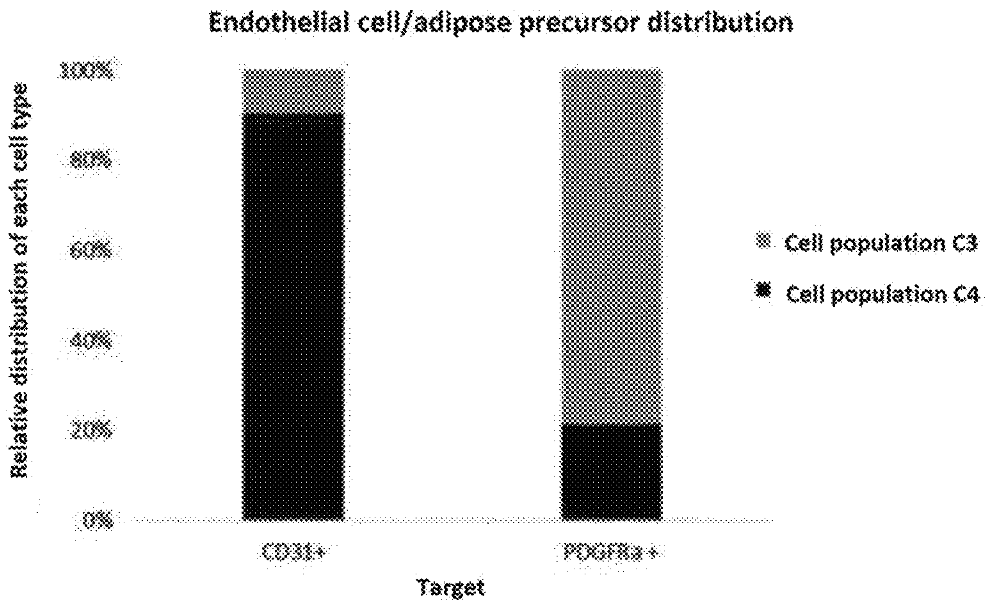
FIG. 6A represents a quantitative PCR of the cell populations C2 and C3 making it possible to determine the relative proportion of CD31+ endothelial cells and of PDGFRa+ adipose tissue stem cells.
Figure 6B:
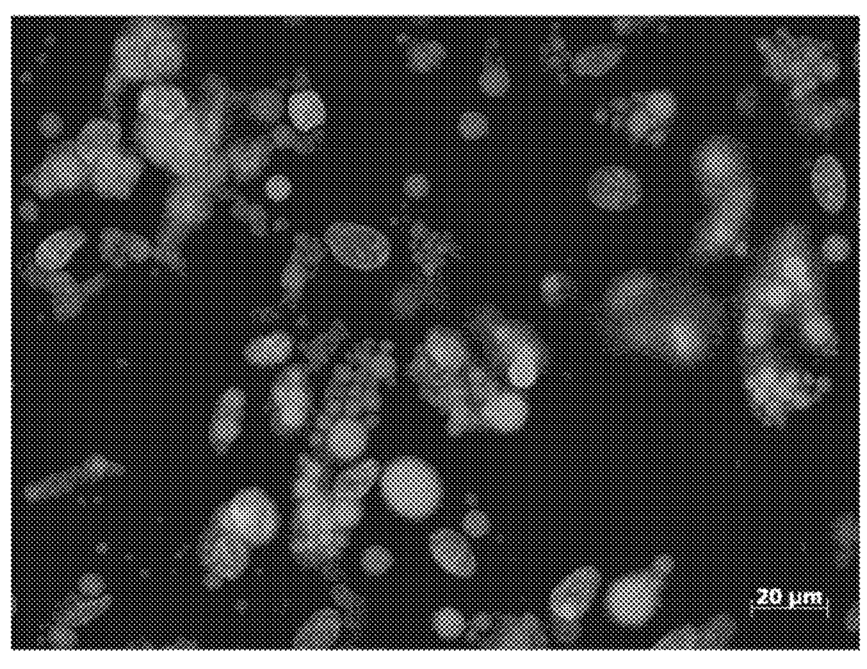
FIG. 6B is a fluorescence microscopy image showing the adipocytic differentiation capacity of the cell populations C2; Nuclei (dark gray) Lipid droplets (light gray)

The cell population obtained in step 3, herein called C2, is composed of CD31+ endothelial type cells forming a capillary type network when maintained in 3D and of PDGFRa+ adipose tissue stem cells (FIG. 4 and FIG. 6A). The cell population C2 has the ability to differentiate into mature adipocytes (FIG. 6B).

Figure 5:
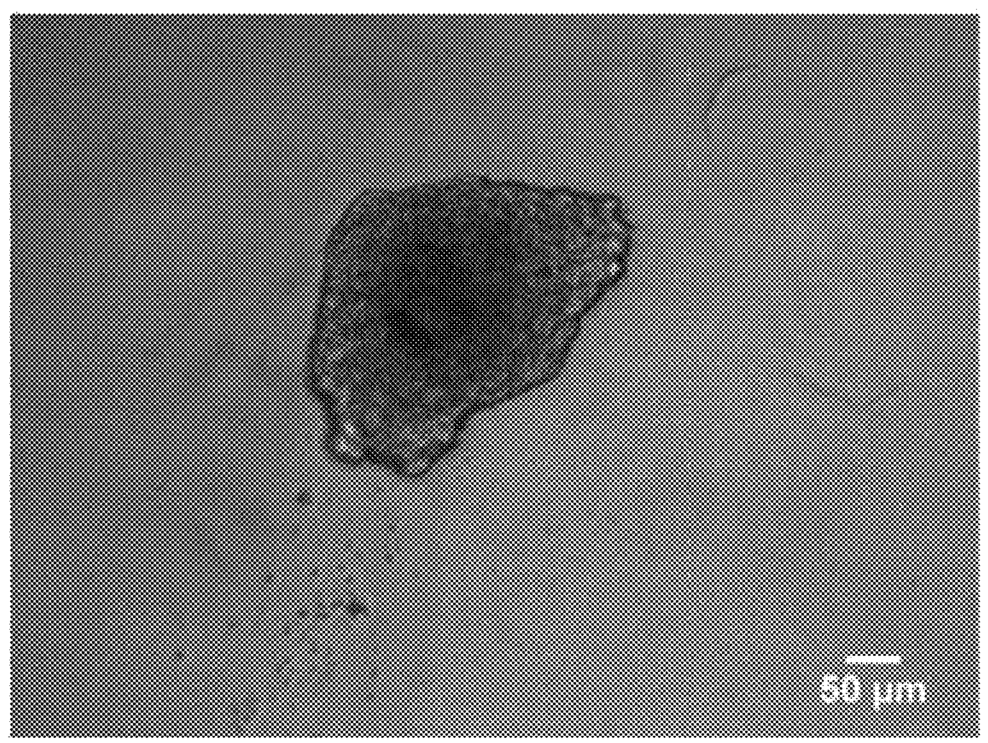
FIG. 5 is a microscopy image of the cell population C3 in EGM+ culture medium in suspension showing the presence of aggregates consisting of PDGFRa+ adipose tissue stem cells.
Figure 6C:
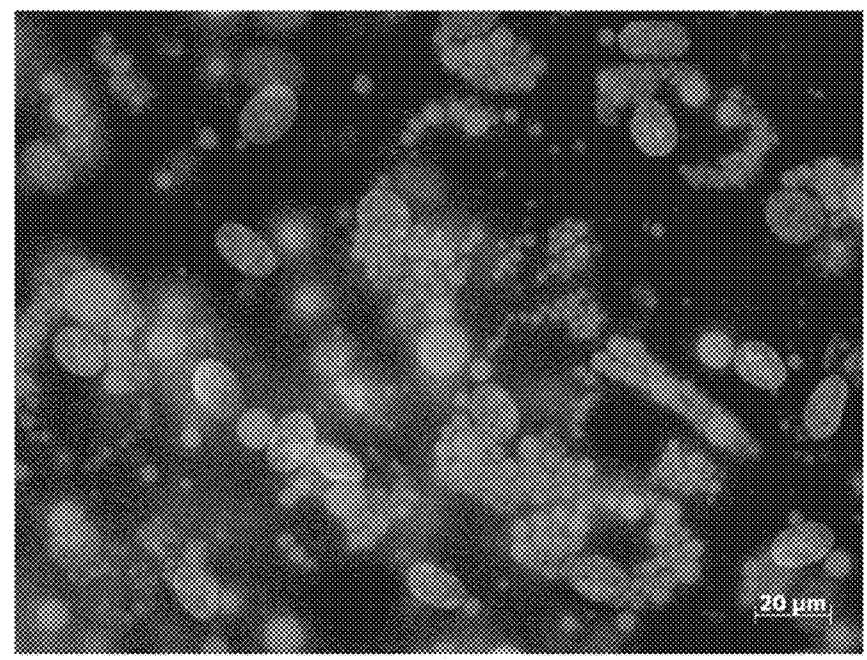
FIG. 6C illustrates, via a fluorescence microscopy image, the adipocytic differentiation capacity of the cell populations C3; Nuclei (dark gray) Lipid droplets (light gray)
Figure 7:
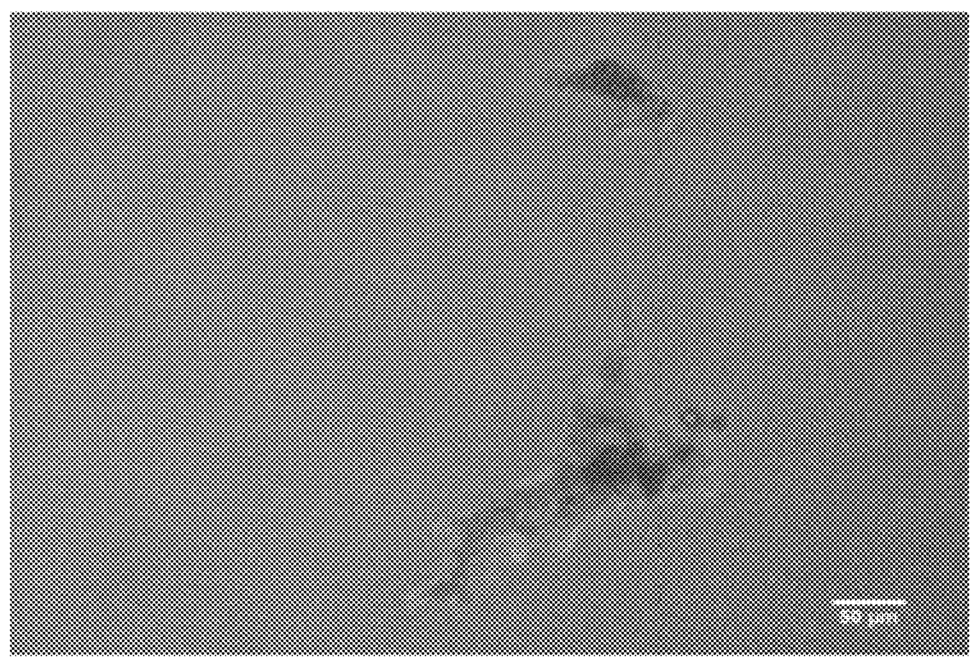
FIG. 7 characterizes, in microscopy, the fibrous type of the matrix M1.

The cell population obtained in step 5, herein called C3, is composed of a majority of PDGFRa+ adipose tissue stem cells capable of forming spheres in suspension (FIG. 5 and FIG. 6A). The cell population C3 has the ability to differentiate into mature adipocytes (FIG. 6C).

c) Characterizing the Matrices M1 to M4 Obtained During the Different Steps of the Method The matrix obtained in step 2, herein called M1 is of the fibrous type (FIG. 7).

Figure 8:
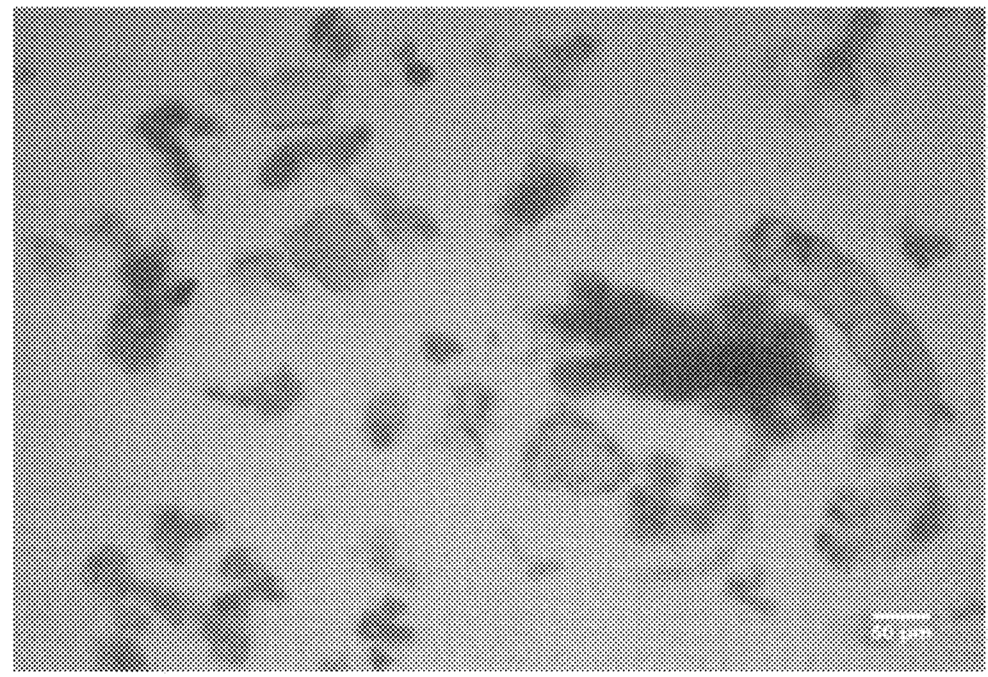
FIG. 8 shows, by microscopy, that the matrix M2 is heterogeneous in terms of matrix types: fibrous type and collagen-rich type.
Figure 10A:
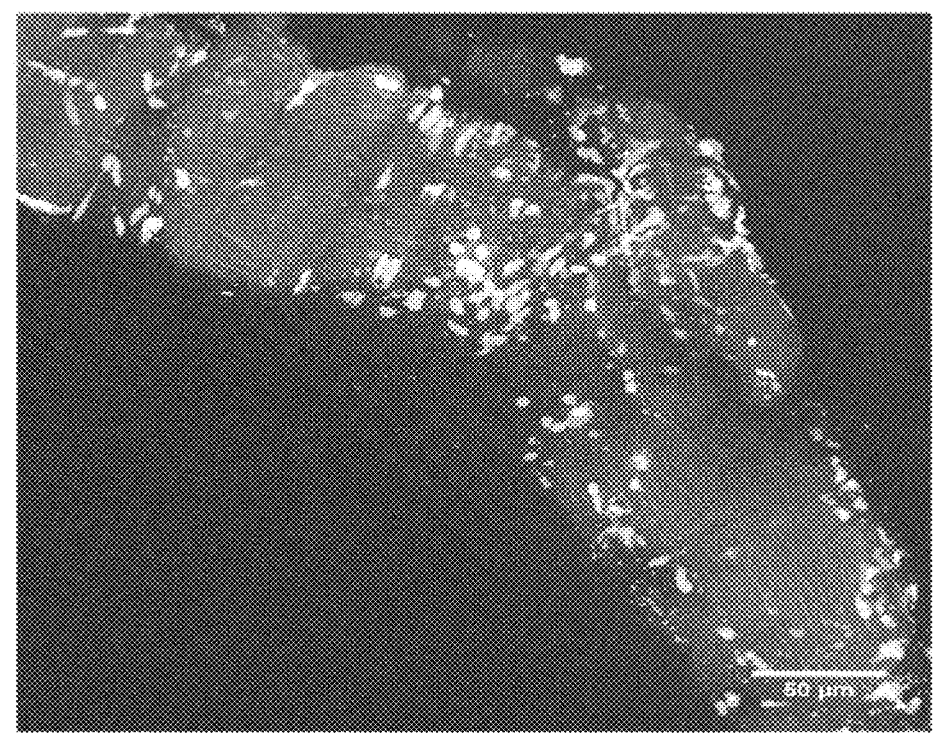
FIG. 10A shows, by fluorescence microscopy, that the matrix M2 is of the collagen-rich type; Picro-Sirius Red-labeled collagen (light gray) and nucleus labeling (white)

The matrix obtained in step 3, herein called M2 is of the fibrous and collagen-rich type (FIG. 8). The collagen is detected with Picro-Sirius Red (FIG. 10A) which makes it possible, furthermore, to view a rod structure of the collagen. This matrix contains endogenous cells.

Figure 9:
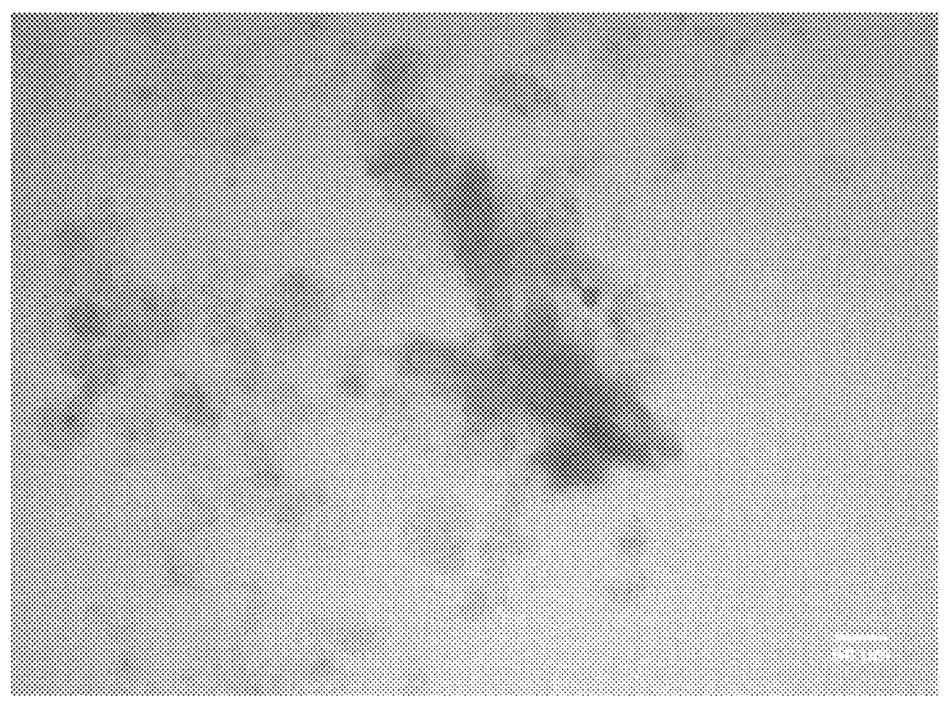
FIG. 9 is a microscopy image illustrating the fibrous type of the matrix M3.
Figure 10B:
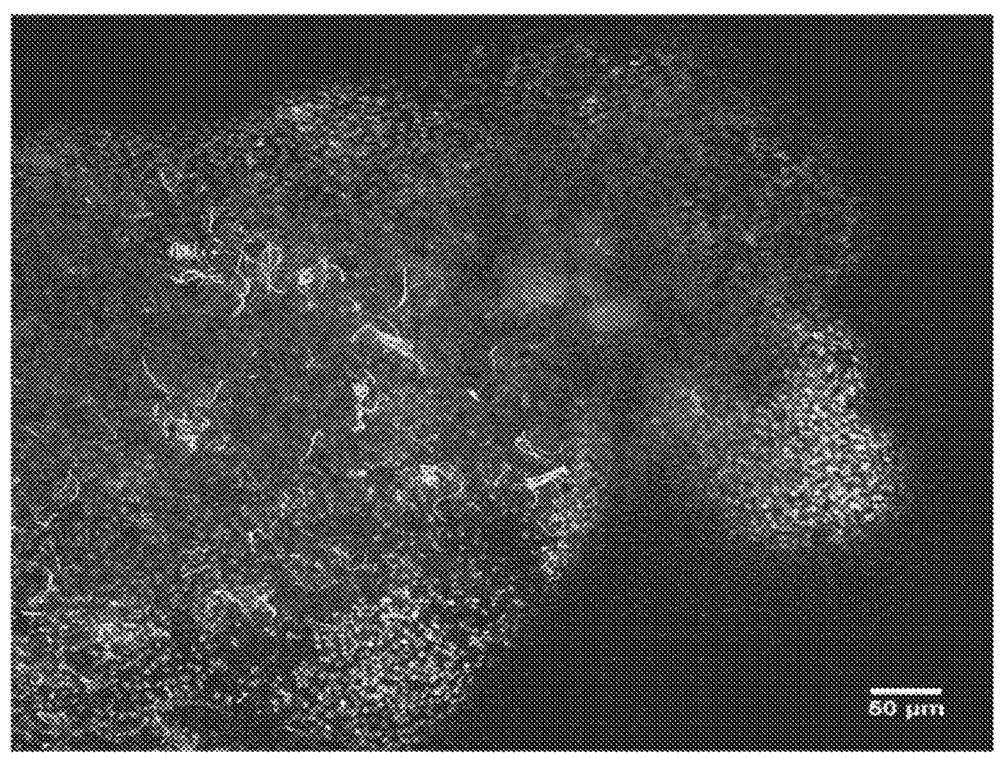
FIG. 10B shows, by fluorescence microscopy, that the matrix M3 is of the fibrous type; Picro-Sirius Red-labeled collagen (light gray and white fibers) and nucleus labeling (white)

The matrix obtained in step 5 and isolated in the collection tube, herein called M3 is of the fibrous type (FIG. 9 and FIG. 10B). This matrix also contains endogenous cells. The collagen from the isolated matrix is detected, in FIG. 10B, with Picro-Sirius Red which stains type I and type III collagen fibers. The red staining (in grayscale in FIG. 10B) obtained indicates that the collagen remains organized, namely that the collagen present always has an α-helix secondary structure and triple-helix quaternary structure. It is not degraded. Indeed, disorganized collagen is stained green by Picro-Sirius Red.

Figure 11A:
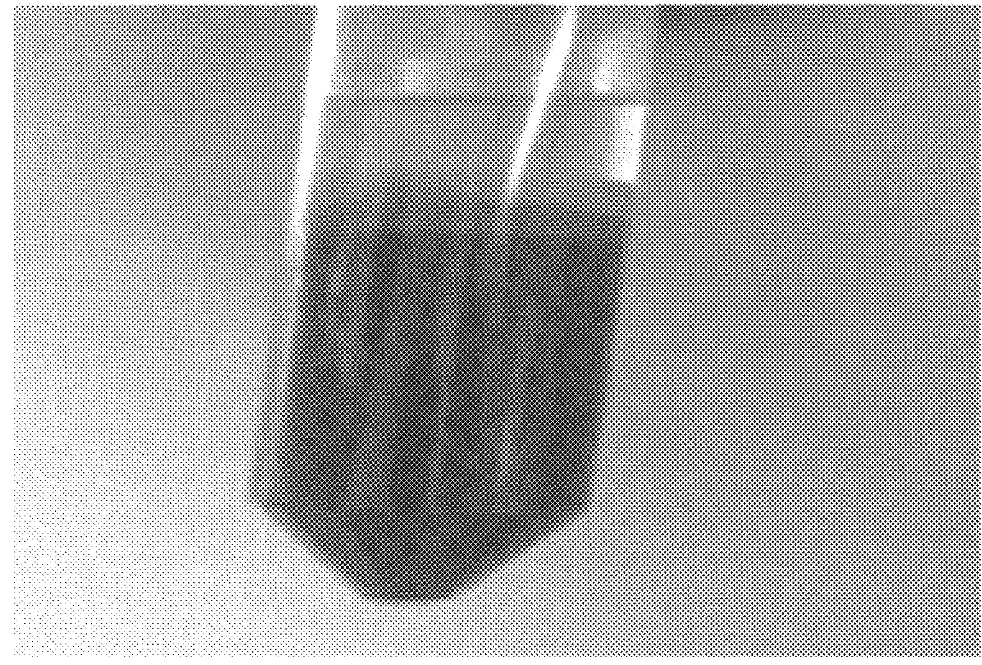
FIG. 11A is a photograph of the centrifuged adipose tissue of the fraction A after mechanical separation containing the matrix M4.
Figure 11B:
FIG. 11B reveals by fluorescence microscopy, in the matrix M4, mature adipocytes by Oil red 0 staining (light gray) and a collagen-rich matrix by type I collagen labeling (very light gray)
Figure 11C:
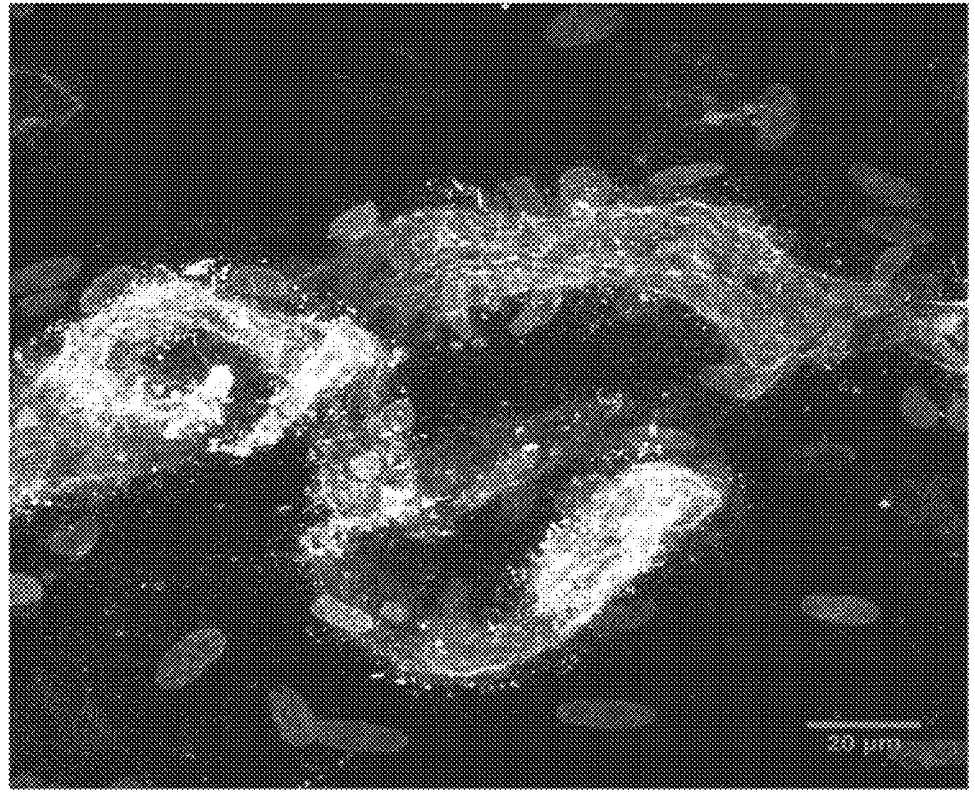
FIG. 11C shows, by CD31 immunolabeling, the capillary structures formed by CD31+ endothelial cells (white) in the matrix M4; nucleus labeling (dark gray)
Figure 11D:
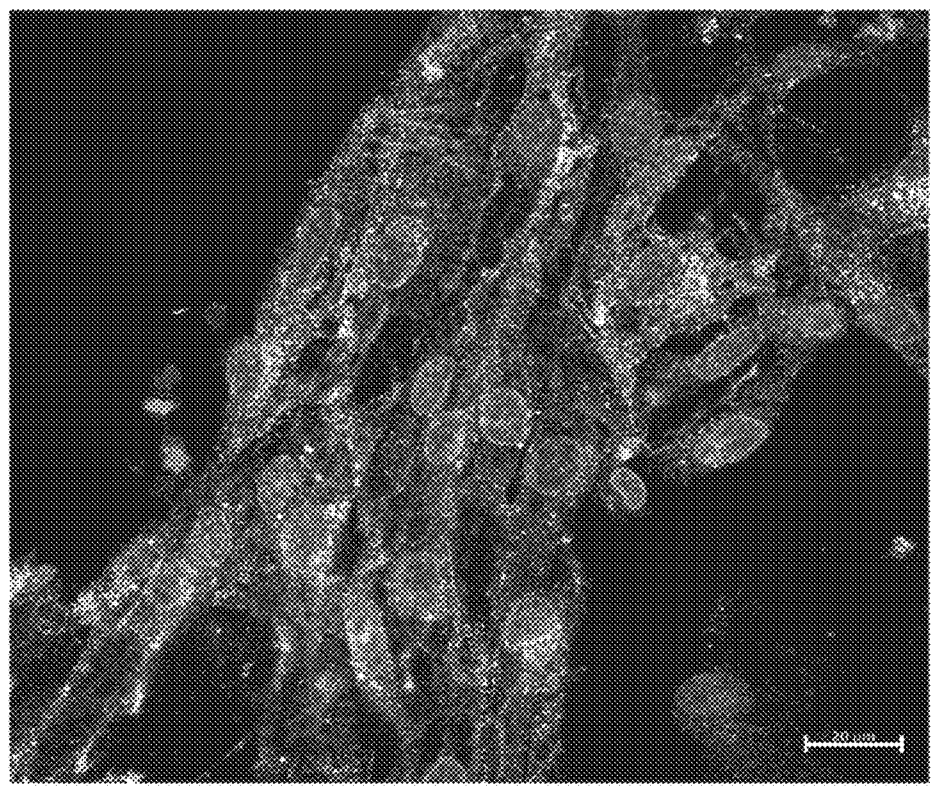
FIG. 11D illustrates the presence of the PDGFRa+ adipose tissue stem cell network (light gray dots) in the matrix M4; nucleus labeling (dark gray)

The matrix obtained in step 5 and contained in the syringe, herein called M4, is composed of a majority of mature adipocytes and a type I collagen framework (FIG. 11B). The matrix M4 is also composed of capillary structures formed by CD31+ endothelial cells (FIG. 11C) and by a PDGFRa+ adipose tissue stem cell network (FIG. 11D).

Figure 1B:
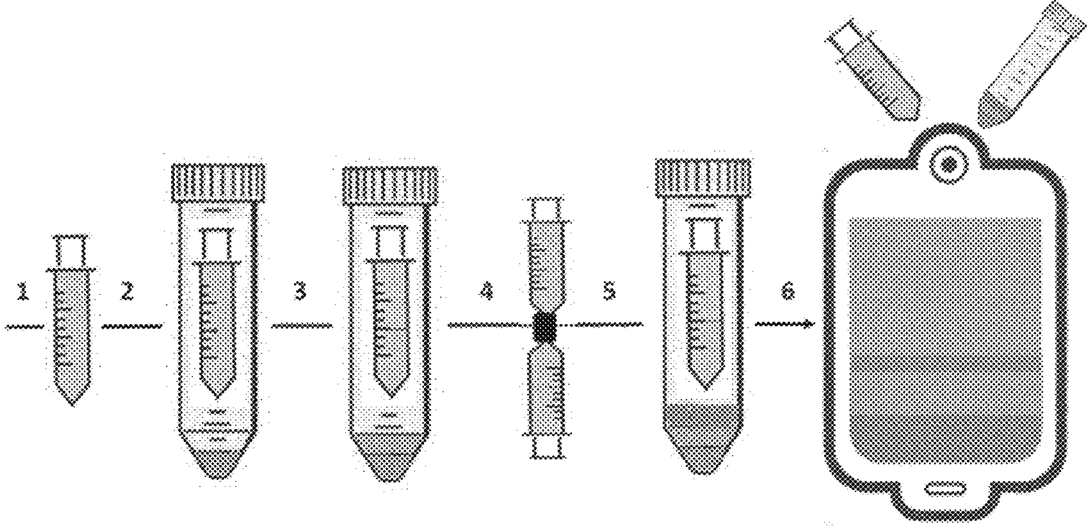
FIG. 1B is a more detailed schematic representation of the method for sequentially extracting extracellular matrices (M1-M4) and stromal vascular fraction cell populations (C1-C3) (steps 1 to 5), and placing them in coculture (step 6), according to the invention.

FIG. 1A shows a method for collecting in step 2 the populations C1 and C2 as well as the matrices M1 and M2. In step 3, the population C3 and the matrices M3 and M4 are grouped together.

Example 2. Cell Expansion and Differentiation

A method for the ex vivo expansion of adipose tissue stem cells and for differentiation in an environment imitating adipose tissue comprises the following steps:

1. The end product obtained in example 1 containing the populations C1-C3 as well as the so-called EndoStem-Matrix matrices M1-M4 are placed in culture in suspension in bags and kept in the EGM+ proliferation medium with stirring for 24 h at 37° C. 5% $CO_2$, then kept under the same conditions, preferably, with stirring.
2. The EGM+ proliferation medium is 50% replaced every two days.

3. A mechanical separation in a closed system, by passing through 2 syringes or two bags of culture in a tulip assembly, is performed on day 5 and day 10.
4. On day 14, the EGM+ proliferation medium is replaced by the differentiation mixture I composed of EGM+ enriched with 250 μM Dexamethasone; 500 μM IBMX; 1 μM Rosiglitazone; 2 μM T3 and 2.5 μg/ml insulin.
5. On day 17, the differentiation medium I is replaced by the differentiation medium II composed of EGM+ enriched with 1 μM Rosiglitazone; 2 μM T3 and 2.5 μg/ml insulin.

Example 3. Characterizing the Amplification Capacity of the Matrix

Figure 12:
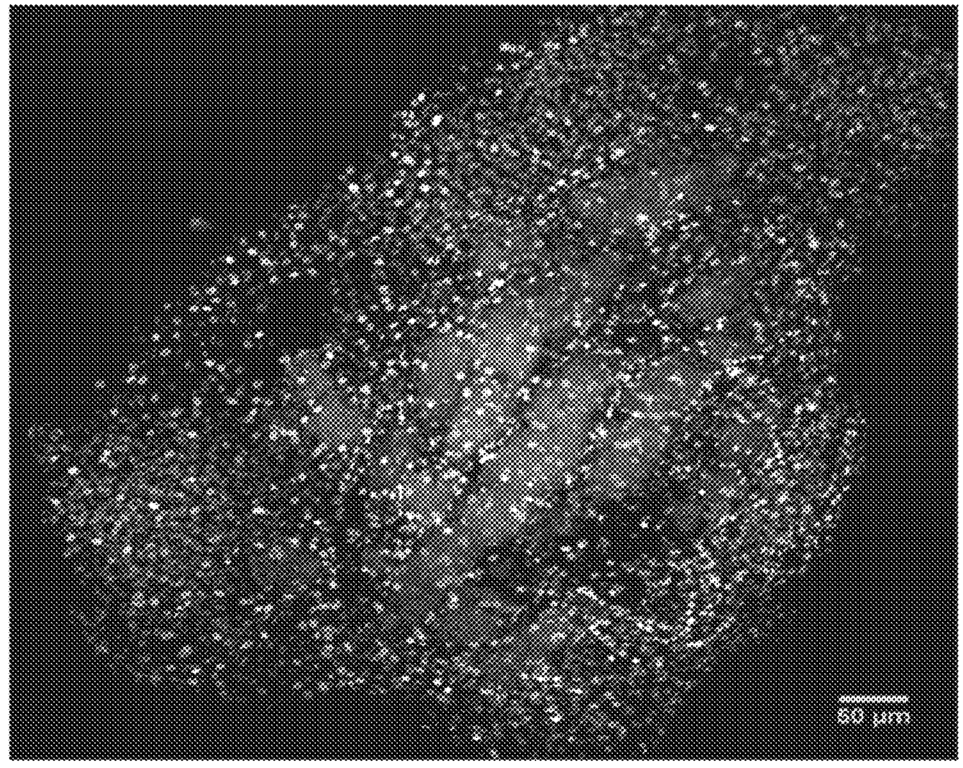
FIG. 12 shows, by incorporating Edu, 5-ethylnyl-2'-deoxyuridine, in the nucleus of the proliferating cells, that the endogenous cells, in the extracellular matrix according to the invention are kept proliferating in the EGM+ medium in suspension; nuclei (dark gray), proliferating cells (white) matrix auto-fluorescence (light gray)

The so-called EndoStem-Matrix extracellular matrices of the invention were characterized, in particular, by fluorescence microscopy, in the presence of different specific markers. Proliferating cells were thus detected by incorporating, during the DNA replication phase, fluorescent Edu (5-ethylnyl-2'-deoxyuridine) in the EndoStem-Matrix matrices of the invention, as illustrated in FIG. 12, proving that the latter are bioactive. Indeed, FIG. 12 shows that the endogenous cells in the matrices are kept proliferating during the amplification phase.

Figure 13:
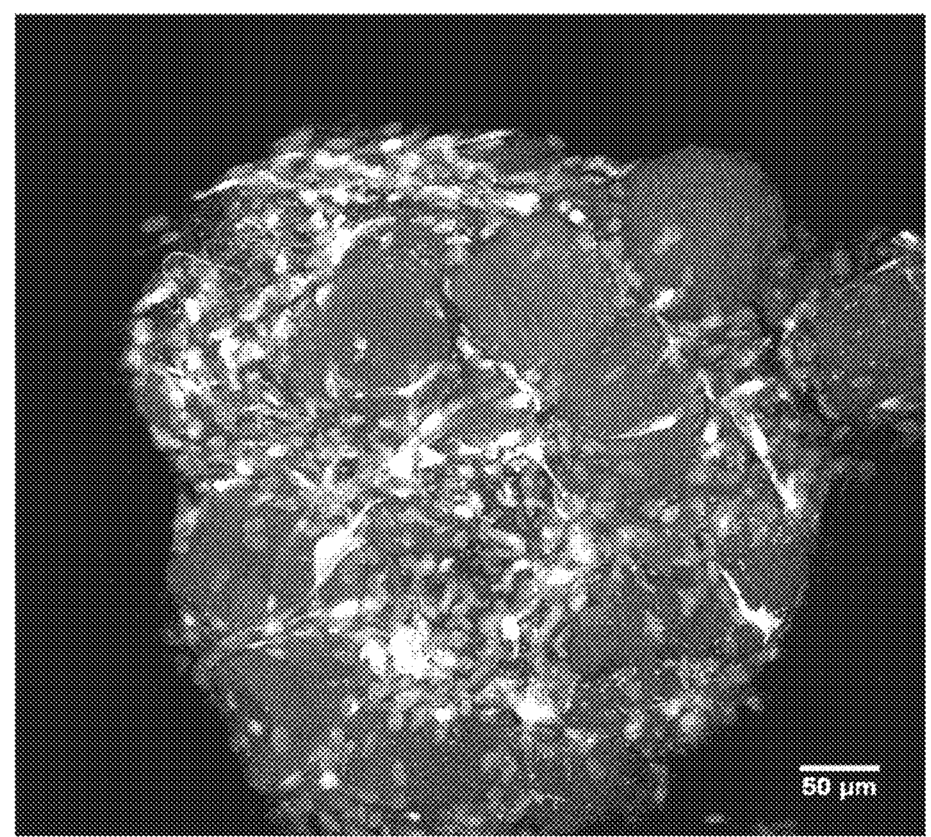
FIG. 13 shows that exogenous adipose tissue stem cells, placed in coculture with the extracellular matrix of the invention, form structures composed of these adipose tissue stem cells and the endogenous cells present in the matrix; image taken after 3 days of coculture, nuclei (dark gray), collagen (light gray), exogenous adipose tissue stem cells (light gray/white)

Moreover, FIG. 13 shows the presence of adipose tissue stem cells after three days of co-culture with the extracellular matrix of the invention. The extracellular matrix therefore makes it possible to supply a substrate for proliferating the stromal vascular fraction: the adipose tissue stem cells added can bind to the EndoStem-Matrix, in suspension.

Figure 14A:
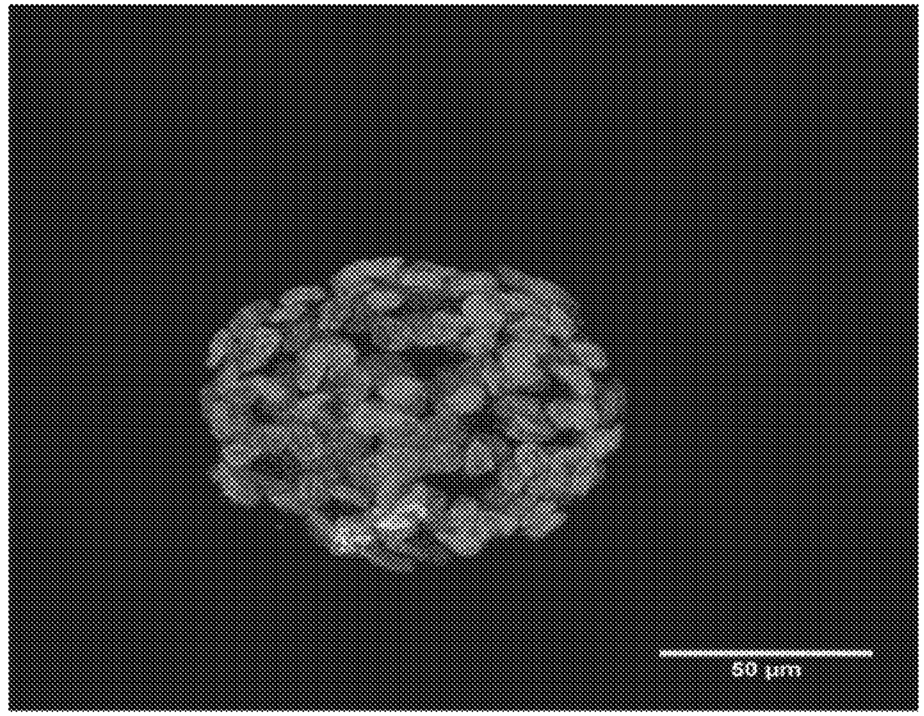
FIG. 14A shows the formation of a cellular aggregate without cell proliferation during the cell culture of adipose tissue stem cells and endothelial cells in suspension without extracellular matrix; image taken after 10 days of coculture; nuclei (dark gray), nuclei of proliferating cells (very light gray)
Figure 14B:
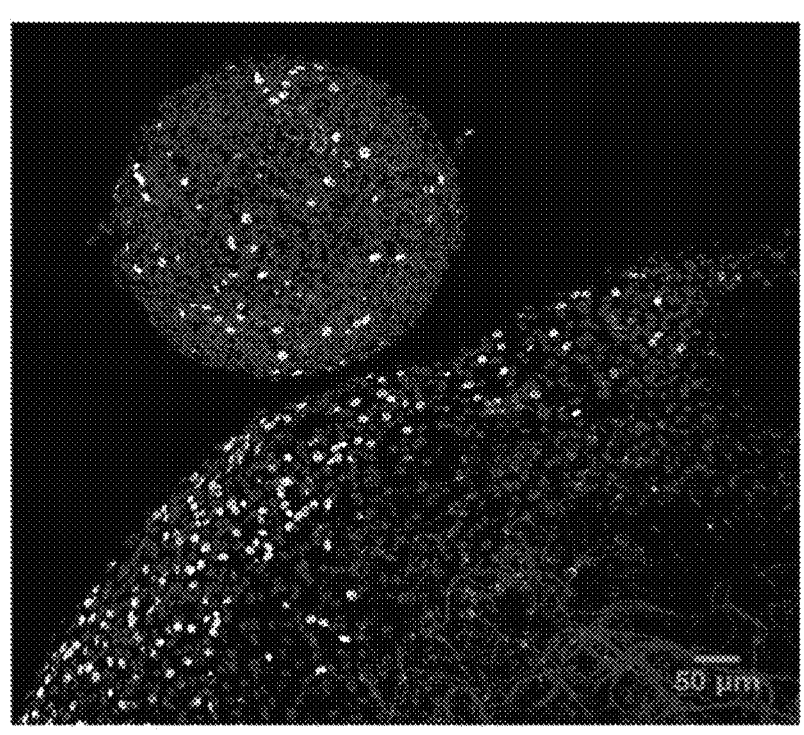
FIG. 14B shows a proliferation capacity of the adipose tissue stem cells and endothelial cells placed in coculture, in suspension, with the extracellular matrix of the invention; image taken after 10 days of coculture; nuclei (dark gray), collagen matrix (light gray), nuclei of proliferating cells by Edu labeling (white)

With reference to FIG. 14B, the stromal vascular fraction is amplified by its culture on the EndoStem Matrix of the invention. Conversely, with reference to FIG. 14A, when the stromal vascular fraction is placed in culture in suspension without the extracellular matrix, cellular aggregates without proliferation are observed. The extracellular matrix of the invention therefore has the ability to amplify the adipose tissue stem cells added.

The cellular amplification capacity of the different matrices M1 to M4 obtained in the steps of example 1 was verified. Thus, about $10^4$ adipose tissue stem cells were kept suspended in the presence of the different matrices M1 to M4 in Ultra-Low Attachment (ULA) wells. Eight days later, the cells are detached from the matrix with trypsin/EDTA then counted. The values obtained are shown in Table 1 below:

TABLE 1

| Conditions | Number of cells | Amplification factor |
|---|---|---|
| Adipose tissue stem cells without matrix | $2 \cdot 10^4$ | 1 |
| Adipose tissue stem cells with matrix M1 | $5 \cdot 10^4$ | 2.5 |
| Adipose tissue stem cells with matrix M2 | $53 \cdot 10^4$ | 26.5 |
| Adipose tissue stem cells with matrix M3 | $7.4 \cdot 10^4$ | 3.7 |
| Adipose tissue stem cells with matrix M4 | $72 \cdot 10^4$ | 36 |
| Matrix M4 without adding adipose tissue stem cells | $5 \cdot 10^4$ | — |

In the table above, for the specific case of the individual matrices M1 to M4, the amplification factor is the ratio between the number of cells obtained after culture in the presence of the extracellular matrix and the number of cells obtained in the absence of the extracellular matrix.

The matrices M2 and M4 have a high adipose tissue stem cell amplification potential. The volume of matrix M2 obtained is very low compared to the volume of M4 (FIG. 11A). The matrix M4 illustrates an extracellular matrix as defined in the invention.

Figure 15A:
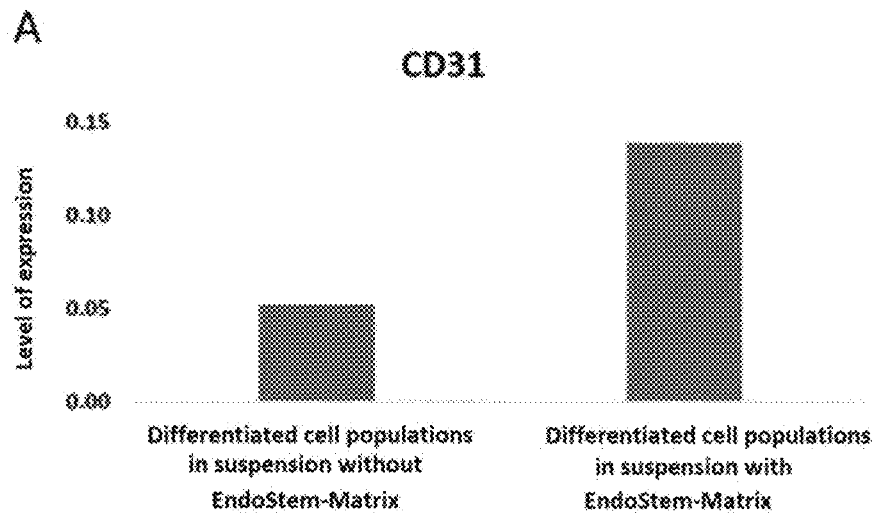
FIG. 15A shows the level of expression of the CD31 endothelial cell marker in the differentiated cell populations obtained by culture, in suspension, with (right) and without (left) the extracellular matrix of the invention.
Figure 15D:
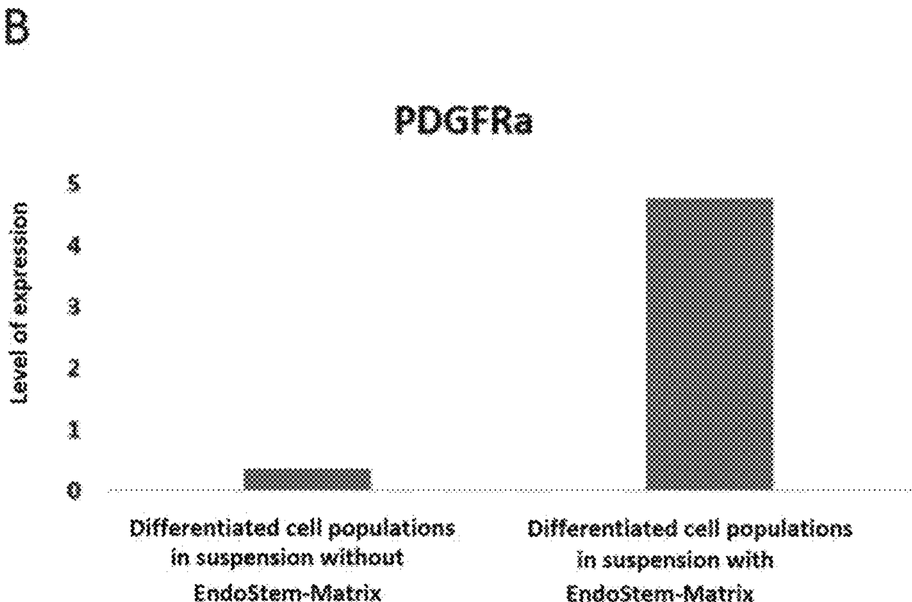
FIG. 15D shows the level of expression of the Adiponectin mature adipocyte marker in the differentiated cell populations obtained by culture, in suspension, with (right) and without (left) the extracellular matrix of the invention.
Figure 15C:
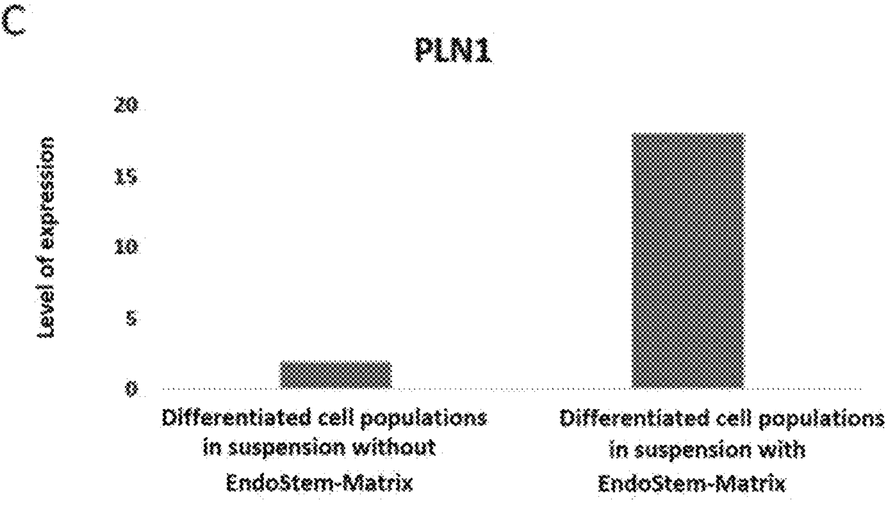
FIG. 15C shows the level of expression of the PLN1 mature adipocyte marker in the differentiated cell populations obtained by culture, in suspension, with (right) and without (left) the extracellular matrix of the invention.
Figure 15B:
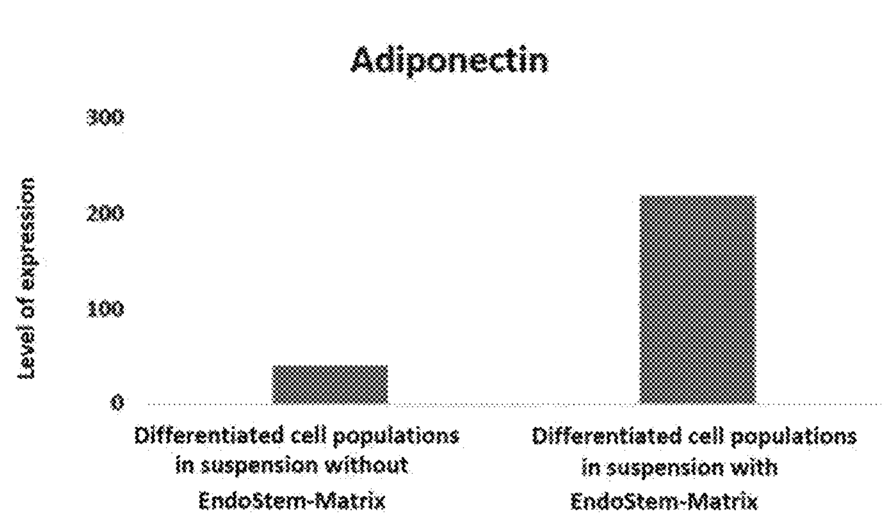
FIG. 15B shows the level of expression of the PDGFRa adipocytic stem cell marker in the differentiated cell populations obtained by culture, in suspension, with (right) and without (left) the extracellular matrix of the invention.

The level of expression of different cell markers (CD31 endothelial cell marker, PDGFRa+ adipocytic stem cell marker, and two PLN1 and Adiponectin mature adipocyte markers) was analyzed after suspension culture of the stromal vascular fraction on the extracellular matrix of the invention. FIG. 15 shows a comparison of these levels of expression with those obtained from a suspension culture of the stromal vascular fraction without the extracellular matrix of the invention. This study shows an amplification of the endothelial cells of the human adipose tissue vascular network (FIG. 15A) and human adipose tissue stem cells (FIG. 15B). This study also makes it possible to demonstrate the superior differentiation capacity induced by the extracellular matrix of the invention (FIGS. 15C and 15D). Thus, the adipose tissue stem cells amplified in 3D on the extracellular matrix of the invention retain their ability to differentiate into adipocytes.

Figure 16:
FIG. 16 represents an image by fluorescence microscopy of the stromal vascular fraction after amplification and differentiation in the presence of the extracellular matrix of the invention; nucleus (dark gray), mature adipocyte (light gray), collagenic matrix (medium gray)

FIG. 16 demonstrates the presence of nuclei, of mature adipocytes and of a collagenic matrix after amplification and differentiation of the stromal vascular fraction in the presence of the extracellular matrix of the invention. Thus, the differentiation in the presence of the extracellular matrix of the invention makes it possible to retain the in vivo structural organization of the adipose tissue.

Figure 17A:
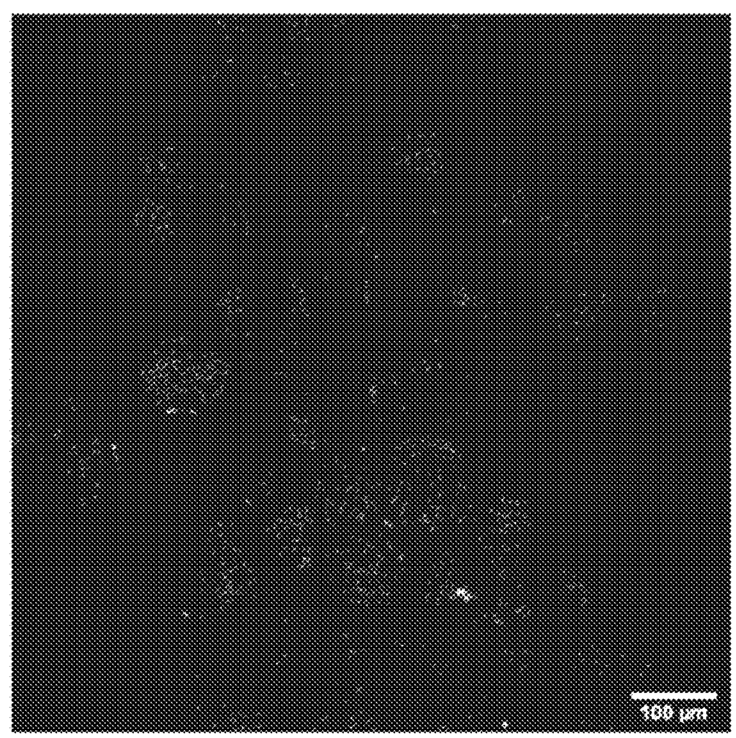
FIGS. 17A and 17B and images showing the activation of the proliferation capacities according to the invention.
Figure 17B:
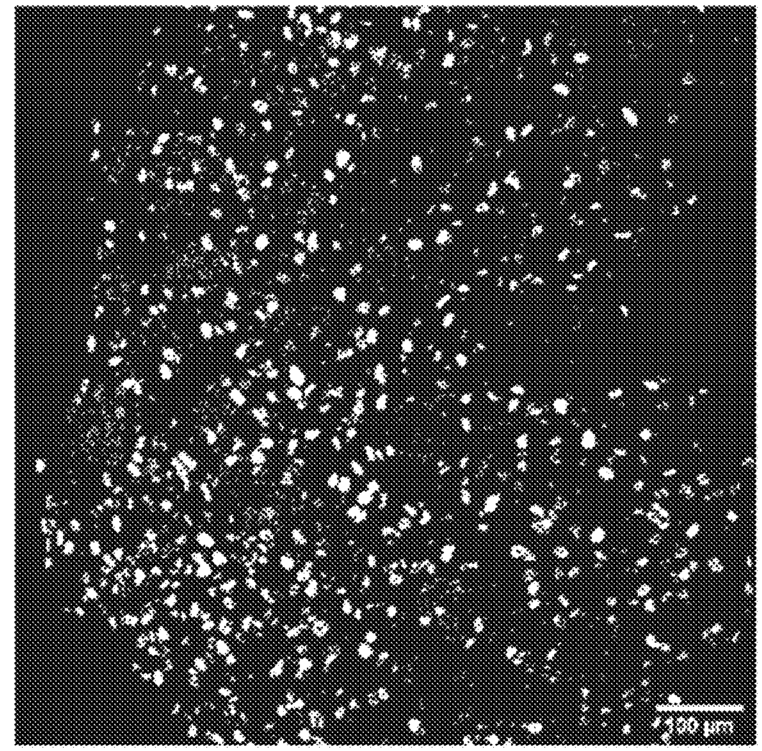

It should be noted that a non-separated adipose tissue, which can be equivalent to an explant, remains viable for a short time ex vivo. Thus, as shown particularly in FIG. 12, the matrix isolated by separation contains proliferating cells, unlike a non-separated tissue. FIGS. 17A and 17B make it possible to compare the cell proliferation in the non-separated tissue (FIG. 17A) and in the isolated matrix (FIG. 17B). In FIG. 17A, the non-separated adipose tissue shows no proliferating cells. In FIG. 17B, the composition shows proliferating cells. Indeed, this figure shows, in white, the nuclei of the proliferating cells.

Figures 18A, 18B, 18C, 18D, 19A, 19B:
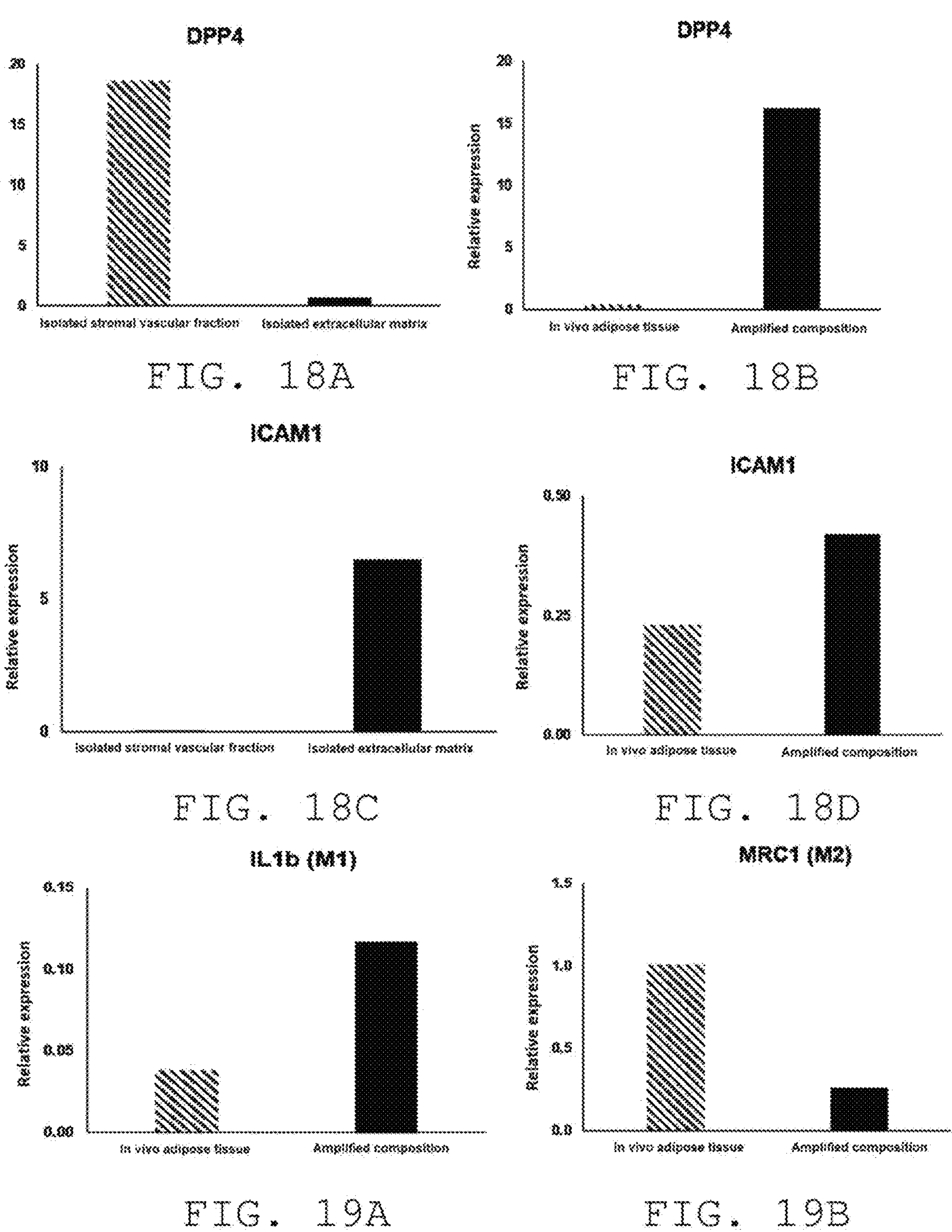
FIGS. 18A, 18B, 18C and 18D, illustrate the expression of dipeptidyl peptidase-4 (DPP4), which is concentrated in the isolated stromal vascular fraction (SVF), and the expression of ICAM1, which is concentrated in the isolated matrix.
FIGS. 19A and 19B illustrate the presence of M1 type and M2 type macrophages respectively, in the amplified composition according to the invention.

It should be noted that the cells isolated according to the invention, by centrifuging the fluid form the washes, are characterized molecularly by the marker DPP4. DPP4 is a marker which labels ICAM1 pre-adipocyte precursor cells, which has a high proliferation capacity and which are located in the interstitial reticulum of the adipose tissue. These cells have the proliferation capacity in the composition according to the invention. It is important to note that these cells are removed following the washes carried out according to the methods of the prior art. As shown in FIGS. 18A and 18B, the expression of DPP4 is concentrated in the isolated SVF fraction. The matrix expresses a small amount. On the other hand, and as shown in FIGS. 18C and 18D, the expression of ICAM1 is concentrated in the isolated matrix. The cells carrying the amplification in the composition are the added cells expressing DPP4.

Moreover, it should be noted that in vivo adipose tissue contains macrophages and that the amplified composition according to the invention maintains the presence of M1 type macrophages, as shown in FIG. 19A and of M2 type macrophages as shown in FIG. 19B. In FIG. 19A, the M1 type macrophages are detected by the marker IL-1b and, in FIG. 19B, the M2 type macrophages are detected by the marker MRC1.

Figure 20:
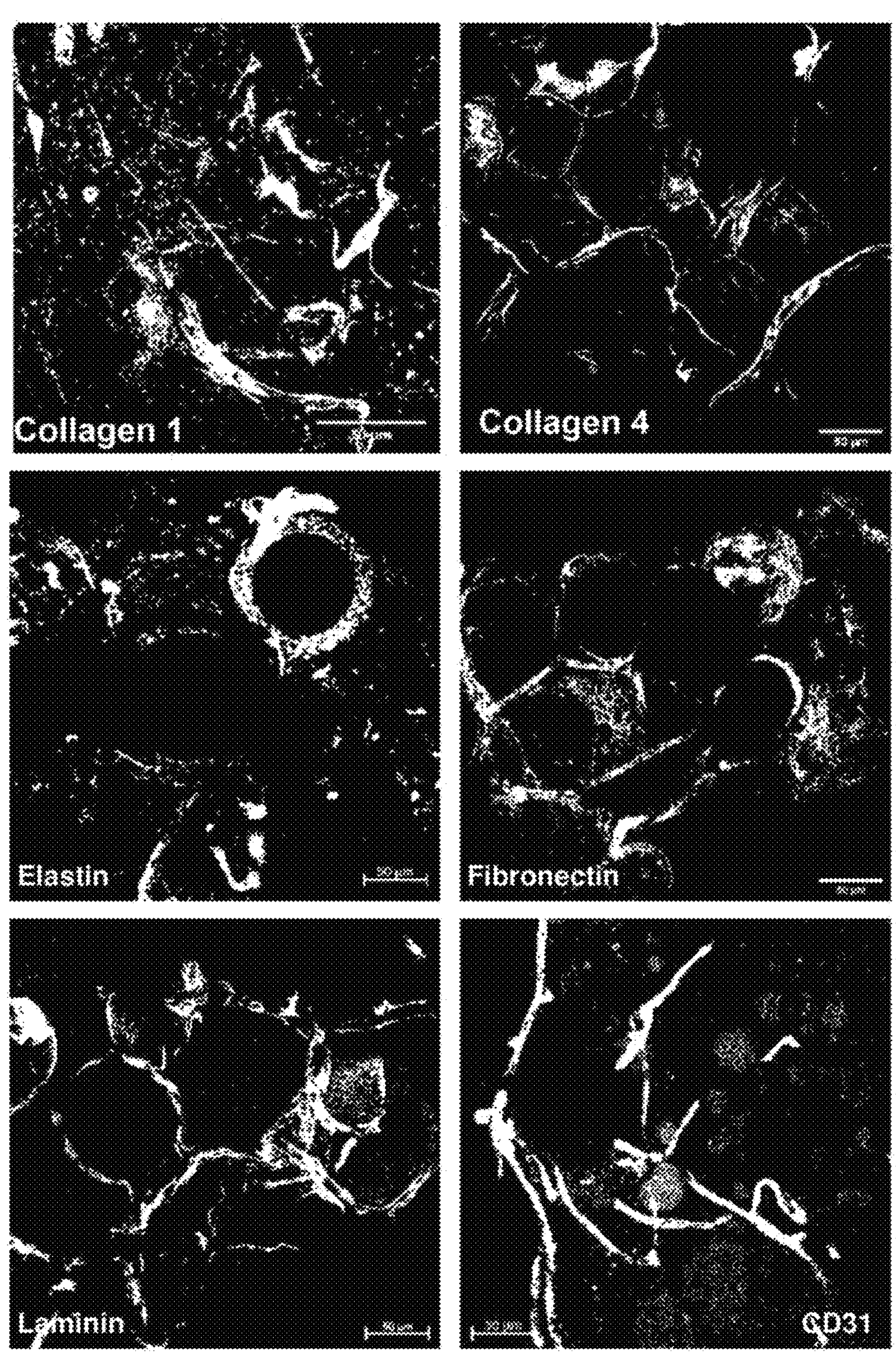
FIG. 20 comprises a set of photographs demonstrating the presence of certain proteins in the extracellular matrix according to the invention, and the preservation of a capillary network.

Finally, and as shown in FIG. 20, the isolated matrix according to the invention comprises extracellular matrix proteins, namely in particular, type I collagen, type IV collagen, elastin, fibronectin, laminin. The labeling of the CD31 endothelial cells shows that a capillary network is retained.

The invention claimed is:

1. A method for in vitro or ex vivo amplification of human adipose tissue stem cells, comprising:

(1) providing a human adipose tissue comprising:
an extracellular matrix comprising collagen,
a vascular network comprising endothelial cells, and
stem cells;

(2) performing extraction, wherein the extraction comprises:

(2a) performing centrifugation of the human adipose tissue to obtain at least two distinct fractions, the at least two distinct fractions including:

a fraction A comprising a centrifuged extracellular matrix fraction, the centrifuged extracellular matrix fraction comprising the extracellular matrix comprising the collagen, and a fraction B comprising a stromal vascular fraction, wherein the stromal vascular fraction comprises cells expressing DPP4, wherein the cells expressing DPP4 in the fraction B constitute a majority of the cells expressing DPP4 initially contained in the provided human adipose tissue, wherein the centrifuged extracellular matrix fraction comprises a first portion of the endothelial cells, and the stromal vascular fraction comprises a second portion of the endothelial cells different from the first portion of the endothelial cells, wherein the centrifuged extracellular matrix fraction comprises a first portion of the stem cells, and the stromal vascular fraction comprises a second portion of the stem cells different from the first portion of the stem cells; and (2b) separating the fraction A from the fraction B, and either (i) performing mechanical dissociation of the fraction A, so as to obtain a fraction A' comprising the extracellular matrix comprising the collagen, wherein the fraction A' comprises the first portion of the endothelial cells and the first portion of the stem cells, mechanically dissociated from the extracellular matrix; or (ii) performing mechanical dissociation of the fraction A, so as to obtain the fraction A' comprising the extracellular matrix comprising the collagen, wherein the fraction A' comprises the first portion of the endothelial cells and the first portion of the stem cells, mechanically dissociated from the extracellular matrix, and further performing centrifugation of the fraction A' to obtain at least two distinct fractions, the at least two distinct fractions including a fraction A" comprising the extracellular matrix comprising the collagen, and a fraction B' comprising the first portion of the endothelial cells and the first portion of the stem cells, (3) mixing the fraction B with either (i) the fraction A' obtained by the mechanical dissociation of the fraction A; or (ii) the fraction B' and the fraction A" obtained by the mechanical dissociation of the fraction A and further centrifugation of the fraction A', to obtain a mixture; and (4) culturing the mixture obtained from the mixing, in suspension, in a culture medium.

2. The method according to claim 1, further comprising: inducing a differentiation of the stem cells to obtain differentiated cells.

3. The method according to claim 2, wherein the differentiated cells are at least one selected from the group consisting of adipocytes and osteoblasts.

4. The method according to claim 3, wherein the differentiated cells are adipocytes.

5. The method according to claim 1, wherein the extraction does not involve collagenase.

6. The method according to claim 5, wherein the mechanical dissociation comprises performing non-enzymatic separation.

7. The method according to claim 1, wherein the collagen of the extracellular matrix is type I collagen and type III collagen.

8. The method according to claim 1, wherein the culturing of the mixture comprises:

transferring the mixture sterilely into a bag of suspension culture comprising culture medium;

amplifying the mixture to form cellular aggregates; and mechanically separating the cellular aggregates.

9. The method according to claim 1, wherein the mechanical dissociation (2b) comprises performing the mechanical dissociation of the fraction A, so as to obtain the fraction A' comprising the extracellular matrix comprising the collagen, and further performing the centrifugation of the fraction A' to obtain the at least two distinct fractions, the at least two distinct fractions including:

the fraction A" comprising the extracellular matrix comprising the collagen, and the fraction B' comprising the first portion of the endothelial cells and the first portion of the stem cells, and the mixing (3) comprises the mixing of the fraction B with the fraction B' and the fraction A" to obtain the mixture.

10. The method according to claim 1, wherein the mechanical dissociation (2b) comprises performing the mechanical dissociation of the fraction A, so as to obtain the fraction A' comprising the extracellular matrix comprising the collagen, and the mixing (3) comprises the mixing of the fraction B with the fraction A' to obtain the mixture.

* * * * *